(12) United States Patent
Sharma et al.

(10) Patent No.: US 10,517,542 B2
(45) Date of Patent: *Dec. 31, 2019

(54) USING BIOMARKER INFORMATION FOR HEART FAILURE RISK COMPUTATION

(71) Applicant: Medtronic, Inc., Minneapolis, MN (US)

(72) Inventors: Vinod Sharma, Maple Grove, MN (US); Eduardo N Warman, Maple Grove, MN (US); Yong K Cho, Excelsior, MN (US); Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 835 days.

This patent is subject to a terminal disclaimer.

(21) Appl. No.: 14/964,529

(22) Filed: Dec. 9, 2015

(65) Prior Publication Data

US 2016/0206250 A1 Jul. 21, 2016

Related U.S. Application Data

(63) Continuation-in-part of application No. 14/798,225, filed on Jul. 13, 2015, now Pat. No. 10,172,568.
(Continued)

(51) Int. Cl.
*A61B 5/00* (2006.01)
*G16H 20/00* (2018.01)
(Continued)

(52) U.S. Cl.
CPC .......... *A61B 5/7275* (2013.01); *A61B 5/0031* (2013.01); *A61B 5/0205* (2013.01);
(Continued)

(58) Field of Classification Search
None
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |

(Continued)

FOREIGN PATENT DOCUMENTS

| | | |
|---|---|---|
| EP | 2008581 | 12/2008 |
| EP | 2 187 807 B1 | 6/2012 |

(Continued)

OTHER PUBLICATIONS

M. Pechenizkiy, "Heart Failure Hospitalization Prediction in Remote Patient Management Systems", et al., 2010 IEEE, pp. 44-49.
(Continued)

*Primary Examiner* — Olivia M. Wise

(57) ABSTRACT

Provided is a method, system and/or apparatus for determining prospective heart failure event risk. Acquired from a device memory are a heart failure patient's current and preceding risk assessment periods. Counting detected data observations in the current risk assessment period for a current risk assessment total amount and counting detected data observations in the preceding risk assessment period for a preceding risk assessment period total amount. Associating the current risk assessment and preceding risk assessment total amounts with a lookup table to acquire prospective risk of heart failure (HF) event for the preceding risk assessment period and the current risk assessment period. Employing weighted sums of the prospective risk of the HF event for the preceding risk assessment period and the current risk assessment period to calculate a weighted prospective risk of the
(Continued)

HF event for a patient. Displaying on a graphical user interface the weighted prospective risk of the HF event for the patient.

6 Claims, 20 Drawing Sheets

Related U.S. Application Data

(60) Provisional application No. 62/024,285, filed on Jul. 14, 2014, provisional application No. 62/037,895, filed on Aug. 15, 2014, provisional application No. 62/091,018, filed on Dec. 12, 2014.

(51) Int. Cl.
| | |
|---|---|
| *G16H 50/30* | (2018.01) |
| *G16H 50/20* | (2018.01) |
| *A61B 5/0205* | (2006.01) |
| *A61B 5/044* | (2006.01) |
| *A61B 5/145* | (2006.01) |
| *G16H 15/00* | (2018.01) |
| *A61B 5/046* | (2006.01) |
| *A61B 5/0464* | (2006.01) |
| *A61B 5/053* | (2006.01) |
| *A61B 5/11* | (2006.01) |

(52) U.S. Cl.
CPC .......... *A61B 5/044* (2013.01); *A61B 5/14503* (2013.01); *A61B 5/14532* (2013.01); *A61B 5/14535* (2013.01); *A61B 5/14546* (2013.01); *A61B 5/4836* (2013.01); *A61B 5/686* (2013.01); *A61B 5/7278* (2013.01); *A61B 5/7435* (2013.01); *A61B 5/7475* (2013.01); *G16H 20/00* (2018.01); *G16H 50/20* (2018.01); *G16H 50/30* (2018.01); *A61B 5/046* (2013.01); *A61B 5/0464* (2013.01); *A61B 5/0537* (2013.01); *A61B 5/1118* (2013.01); *A61B 5/6869* (2013.01); *A61B 2505/07* (2013.01)

(56) References Cited

U.S. PATENT DOCUMENTS

| | | | |
|---|---|---|---|
| 5,545,186 A | 8/1996 | Olson et al. |
| 5,755,736 A | 5/1998 | Gillberg et al. |
| 7,013,176 B2 | 3/2006 | Ding et al. |
| 7,127,290 B2 | 10/2006 | Girouard et al. |
| 7,682,316 B2 | 3/2010 | Anderson et al. |
| 7,986,994 B2 | 7/2011 | Stadler et al. |
| 8,036,749 B2 | 10/2011 | Ziegler et al. |
| 8,052,611 B2 | 11/2011 | Wariar et al. |
| 8,255,046 B2 | 8/2012 | Sarkar et al. |
| 8,346,360 B2 | 1/2013 | Libbus et al. |
| 8,435,186 B2 | 5/2013 | Hettrick et al. |
| 8,478,400 B2 | 7/2013 | Hettrick et al. |
| 8,639,328 B2 | 1/2014 | Hettrick et al. |
| 8,688,469 B2 | 4/2014 | Ziegler et al. |
| 8,744,565 B2 | 6/2014 | Zielinski et al. |
| 8,768,718 B2 | 7/2014 | Cazares et al. |
| 8,777,850 B2 | 7/2014 | Cho et al. |
| 8,831,721 B2 | 9/2014 | Hettrick et al. |
| 8,914,101 B2 | 12/2014 | Hettrick et al. |
| 8,938,292 B2 | 1/2015 | Hettrick et al. |
| 8,948,868 B2 | 2/2015 | Vitense et al. |
| 10,092,186 B2 | 10/2018 | Hatlestad et al. |
| 2007/0288059 A1 | 12/2007 | Davenport et al. |
| 2008/0103530 A1 | 5/2008 | Vitense et al. |
| 2008/0119903 A1 | 5/2008 | Arcot-Krishnamurthy et al. |
| 2008/0228090 A1 | 9/2008 | Wariar et al. |
| 2009/0125328 A1 | 5/2009 | Nevins |
| 2009/0270933 A1 | 10/2009 | Hettrick et al. |
| 2009/0275855 A1 | 11/2009 | Zielinski et al. |
| 2010/0030087 A1 | 2/2010 | Hettrick et al. |
| 2010/0030292 A1 | 2/2010 | Sarkar et al. |
| 2010/0030293 A1 | 2/2010 | Sarkar et al. |
| 2010/0113888 A1 | 5/2010 | Cho et al. |
| 2010/0113962 A1 | 5/2010 | Hettrick et al. |
| 2010/0204550 A1 | 8/2010 | Heneghan et al. |
| 2012/0109243 A1 | 5/2012 | Hettrick et al. |
| 2012/0109245 A1 | 5/2012 | Hettrick et al. |
| 2012/0109675 A1 | 5/2012 | Ziegler et al. |
| 2012/0253207 A1 | 10/2012 | Sarkar et al. |
| 2012/0303085 A1 | 11/2012 | Vitense et al. |
| 2013/0030319 A1 | 1/2013 | Hettrick et al. |
| 2013/0197599 A1 | 8/2013 | Sambelashvili et al. |
| 2014/0288455 A1 | 9/2014 | Zielinski et al. |
| 2015/0088216 A1 | 3/2015 | Gordon et al. |
| 2015/0126883 A1 | 5/2015 | An et al. |
| 2015/0230722 A1 | 8/2015 | Sarkar et al. |

FOREIGN PATENT DOCUMENTS

| | | |
|---|---|---|
| WO | WO 2009036329 | 3/2009 |
| WO | 2011053434 A1 | 5/2011 |
| WO | WO11126823 | 10/2011 |
| WO | WO2012135775 | 10/2012 |

OTHER PUBLICATIONS (PCT/US2015/040383) PCT Notification of Transmittal of the International Search Report and the Written Opinion of the International Searching Authority, dated Oct. 14, 2015, 11 pages.

Martin R. Cowie et al., "Development and validation of an integrated diagnostic algorithm derived from parameters monitored in implantable devices for identifying patients at risk for heart failure hospitalization in an ambulatory setting", European Heart Journal (2013), 34, 2472-2480.

U.S. Appl. No. 13/391,376, filed Mar. 29, 2011.

(PCT/US2016/065768) PCT Notification of Transmittal of the International Search Report and the Written Opinion of the International Searching Authority, dated Mar. 16, 2017, 10 pages.

130

Heart Failure Report — 132

| Device Name | Serial Number | Date |
| Patient | | Physician |

134 → Date of Birth     Hospital
History

136 CLINICAL STATUS

| Treated VT/VF | 0 episodes | Treated VT/VF | 83.3% |
| AT/AF | 5 episodes | AT/AF | 40.1% |
| Time in AT/AF | 5.4 hr/day (22.3%) | | |

144 →

138 TREND SUMMARY        HIGH RISK

96   Fluid Index (max value) ← 142A

● AT/AF:    28 Days with 24 Hr AT/AF ← 142B
    V. Rate during AT/AF

140 → ● Activity    Less than 1 hr/day for 4 weeks ← 142C
    Heart Rate
    Heart Rate Variability ● V. Pacing    Less than 90% ← 142D
    Shock(s)

Fig. 6

| Diagnostic Variable | Default Threshold Value |
|---|---|
| OptiVol Index (Ω-days) | 60 Ω-days |
| Impedance (Ω) | None |
| AT/AF (hrs/day) | Time in AT/AF is greater than or equal to 6 hrs for at least 1 day |
| V-rate during AT/AF (bpm) | Time in AT/AF is greater than or equal to 6 hrs for at least 1 day |
| Activity (hrs/day) | Average Activity for at least 1 week is < 1 hr/day |
| V Rate (bpm) | Night Heart Rate (NHR) > 85 bpm for all of the most recent 7 days |
| HRV (ms) | None |
| % Pacing | V-pacing < 90% since last session (only applicable to CRT devices) |

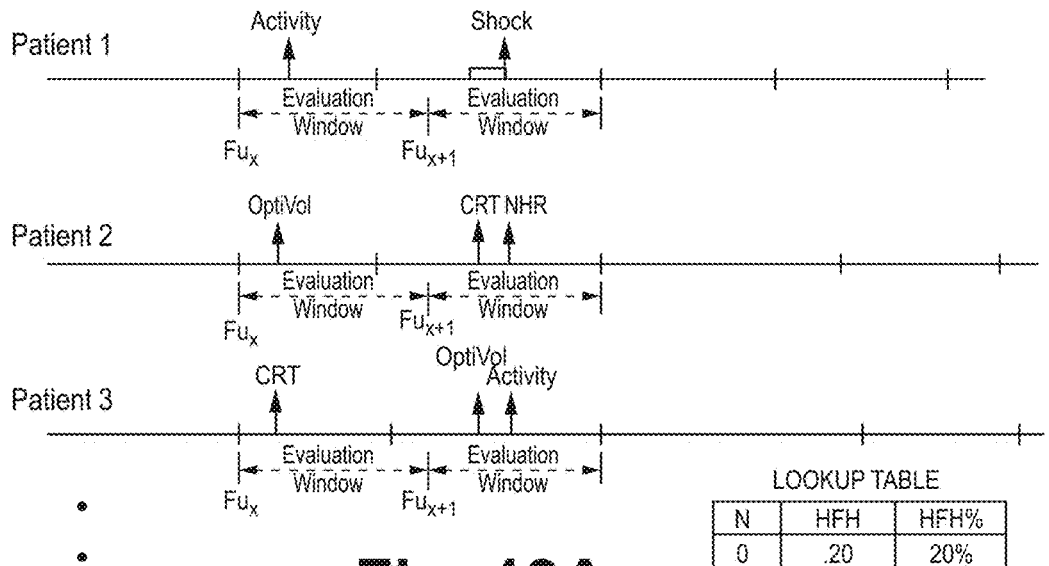
Fig. 13A
Fig. 13C
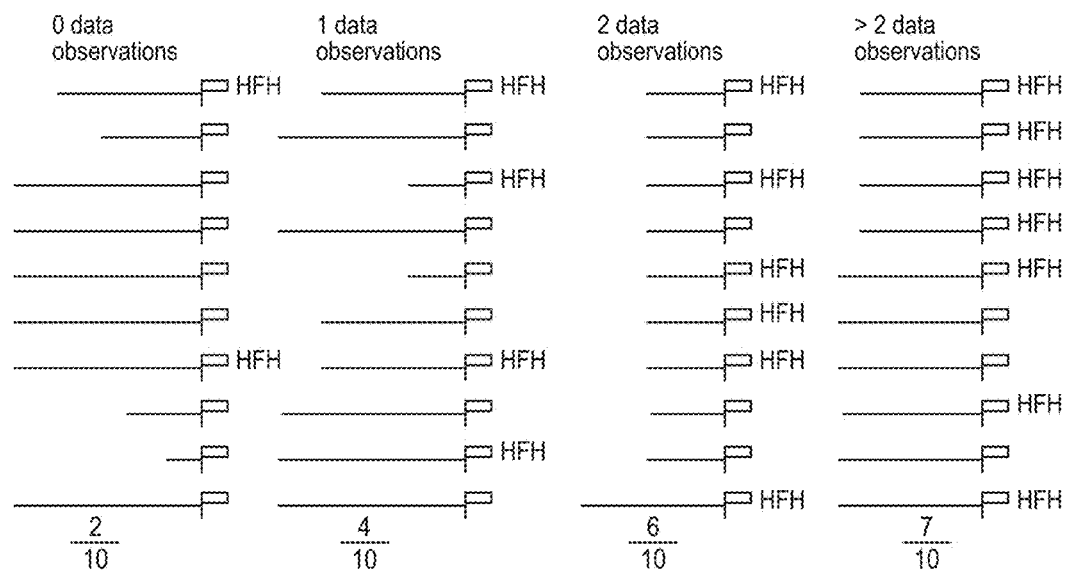
Fig. 13B

Fig. 15

Proposed Screen

| Overview | Alert Groups | Red Alert Clinic Notification | Yellow Alert Clinic Notification | Notification Hours |

☐ Display descriptions of alert conditions

| Clinical Management Alerts | ● Red Alert | ● Yellow Alert | Website-only Alert |
|---|---|---|---|
| AT/AF Daily Burden > Threshold | ○ | ● | ○ |
| Average Ventricular Rate during AT/AF | ○ | ● | ○ |
| Number of Shocks Delivered in an Episode | ○ | ● | ○ |
| All Therapies in a Zone Exhausted | ● | ○ | ○ |
| Multiple clinical events. Show Publication Alert will be triggered if all checked events have occurred during a transmission. Or, if a given number of events have occurred. Check ALL Events | ○ | ○ | ● |
| ☐ Time in AT/AF ≥ [xxx] hours for at least 1 day | | | |
| ☑ Time in AT/AF ≥ [xxx] hours and Mean V-Rate > [yyy] for at least one day | | | |
| ☐ NHR > 85 bpm for all of the most recent 7 days | | | |
| ☑ Average activity for at least 1 week is < 1 hour/day | | | |
| ☑ At least one VT/VF Shock | | | |
| ☑ VP<90% since last transmission (only visible for CRT devices) | | | |
| ___ Events have occurred from selected list | | | |

| Lead/Device Integrity Alerts | ● Red Alert | ● Yellow Alert | Website-only Alert |
|---|---|---|---|
| VF Detection/Therapy Off | ● | ○ | ○ |
| Low Battery Voltage Recommended Replacement Time | ○ | ● | ○ |
| Excessive Charge Time End of Service | ● | ○ | ○ |
| Right Ventricular Lead Integrity | ● | ○ | ○ |
| Right Ventricular Lead Noise | ● | ○ | ○ |
| Atrial Pacing Impedance Out of Range | ○ | ● | ○ |
| Right Ventricular Pacing Impedance Out of Range | ● | ○ | ○ |

USING BIOMARKER INFORMATION FOR HEART FAILURE RISK COMPUTATION

CROSS-REFERENCE TO RELATED APPLICATIONS

This application claims the benefit of U.S. patent application Ser. No. 14/798,225 filed on Jul. 13, 2015, which claimed the benefit of U.S. Provisional Application No. 62/024,285, filed on Jul. 14, 2014. The disclosure of the above application is incorporated herein by reference in its entirety. This application further claims the benefit of U.S. Provisional Application No. 62/037,895, filed on Aug. 15, 2014. The disclosure of the above application is incorporated herein by reference in its entirety.

TECHNICAL FIELD

The present disclosure relates to medical devices, and, more particularly, to medical devices that monitor cardiac health.

BACKGROUND

Chronic heart failure (HF) occurs when a heart is unable to consistently pump blood at an adequate rate in response to the filling pressure. To improve the ability of the heart to pump blood, congestive heart failure patients, classified as having New York Heart Association (NYHA) class status of II to IV HF, may require implantable medical devices (IMDs) such as implantable cardioverter defibrillators (ICDs) and cardiac resynchronization devices with defibrillation capability (CRT-Ds). Despite using IMDs to improve heart function, some HF patients may require hospitalization. Global health care systems incur billions of dollars each year due to heart failure hospitalizations (HFHs). Identifying patients at risk of HFH to enable timely intervention and prevent expensive hospitalization remains a challenge. Implantable cardioverter defibrillators (ICDs) and cardiac resynchronization devices with defibrillation capability (CRT-Ds) are configured to acquire data for a variety of diagnostic metrics that change with HF status and collectively have the potential to signal an increasing risk of HFH. Diagnostic parameter data collected by IMDs include activity, day and night heart rate (NHR), atrial tachycardia/atrial fibrillation (AT/AF) burden, mean rate during AT/AF, percent CRT pacing, number of shocks, and intrathoracic impedance. Additionally, preset or programmable thresholds for diagnostic metrics, when crossed, trigger a notification, referred to as device observation. Each device observation is recorded in an IMD report.

One conventional method for predicting HFH risk is US pregrant publication No. 2012/0253207 A1, entitled Heart Failure Monitoring, to Sarkar et al. Sarkar et al. is directed to a post-discharge period in which the IMD is interrogated remotely through wireless transmission to evaluate the prognosis of the patient using device diagnostics. For example, an evaluation can be performed during a 7 day period post discharge such that a determination is made as whether the patient had 1-6 days of AF burden>6 hrs, poor rate control (i.e. 1 day of AF>6 hrs and rate>90 bpm), a fluid index greater than 60 or 100 ohm-days, night heart rate>85 bpm, heart rate variability less than or equal to 40 ms, ventricular tachycardia, or % CRT pacing<90%. If any two of the listed parameters were met, the patient is considered high risk for a re-admission and is designated for post discharge care (e.g. nurse call or treatment modifications). If no criterion is met, the patient is considered at lower risk for HFH and less attention is provided to that patient. While Sarkar et al. provides useful information as to calculating the risk of HFH, it is desirable to provide gradations of HFH risk. Additionally, it is also desirable to provide develop a method that simplifies the HFH risk calculation without regard as to whether two different listed parameters were triggered.

Another method for estimating HFH risk is disclosed in a risk stratification study by Martin R. Cowie et al., *Development And Validation Of An Integrated Diagnostic Algorithm Derived From Parameters Monitored In Implantable Devices For Identifying Patients At Risk For Heart Failure Hospitalization In An Ambulatory Setting Which Disclosed That Various IMD Diagnostics Variables Could Be Combined For The Previous 30-Days Using A Heuristic Approach To Assess Patient HF Risk In The Next 30 Days*, European Heart Journal (Aug. 14, 2013) (hereinafter referred to as the EHJ article).

Yet another method involves U.S. Pat. No. 8,768,718 B2 to Cazares et al. Cazares et al. uses between-patient comparisons for risk stratification of future heart failure decompensation. Current patient data is collected by a patient monitoring device. A reference group related to the patient is determined. A reference group dataset is selected from the reference group. The dataset includes patient data that is of a similar type received from the patient monitoring device. A model of the reference group dataset is generated using a probability distribution function and automatically compared to the received physiological data to a model to derive an index for the patient. This method is cumbersome. For example, the method requires a model of the reference group dataset is generated and automatically compared using a probability distribution function. Numerous other methods include various complexities such as U.S. Pat. No. 8,777,850 to Cho et al., US Pregrant Application 2012/0109243 to Hettrick et al. U.S. Pat. No. 7,682,316 B2 to Anderson et al.

While a number of methods can be used to predict HFH risk, improvements can be made. For example, it is desirable to develop a method to estimate risk of HFH that can be easily implemented without unduly burdening healthcare providers. Additionally, it would be desirable to have a method or system that was able to present increased gradations of HFH risk instead of broad risk categories such as high risk and low risk.

BRIEF DESCRIPTION OF DRAWINGS

FIG. 6 illustrates an example user interface that includes exemplary heart failure data that may be used in determining heart failure hospitalization for a patient.

FIG. 9 depicts a diagnostic variable and an exemplary default threshold value.

FIG. 12 is a graphical user interface depicting device and clinical events cardiovascular alerts as associated with increasing risk.

FIGS. 13A-13C relate to formation of a database in which a lookup table for prospective heart failure risk is generated. FIG. 13A depicts a set of timelines in which data observations are triggered for a set of patients. FIG. 13B depicts a set of data observation categories associated with heart failure hospitalizations for predicting prospective heart failure hospitalizations. FIG. 13C is a lookup table created to associate total data observations during an evaluation period with prospective heart failure hospitalization.

FIG. 15 is a graphical user interface depicting device and clinical events cardiovascular alerts that can be displayed to a user.

DETAILED DESCRIPTION

Figure 1:
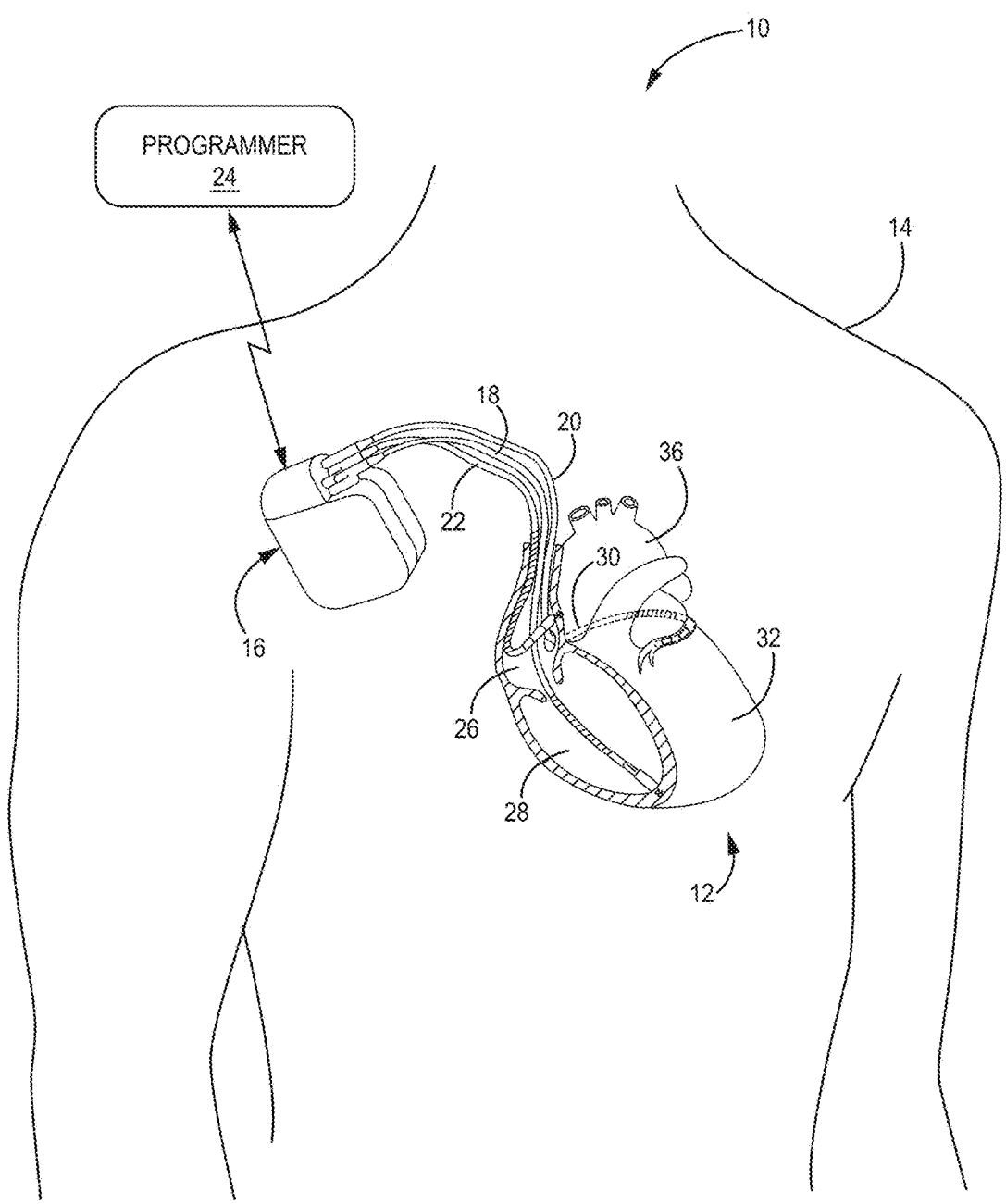
FIG. 1 is a conceptual drawing illustrating an example system configured to transmit diagnostic information indicative of heart failure that includes an implantable medical device (IMD) coupled to implantable medical leads.

Techniques are presented in which a medical device system, using data, customarily acquired through the use of an implantable medical device (IMD), predicts a patient's risk of heart failure hospitalization (HFH). The medical system includes an external device (e.g. server etc.) that is accessed when predicting a patient's risk of HFH. The external device has a collection of heart failure patient-related data organized and stored in memory for access through a processor.

Multiple operations are involved in collecting patient data. Data is interpreted to include datum, the singular form of data, or the plural form of data. Data is typically collected from each patient through an implantable medical device or other suitable means. Techniques described herein focus on data observations measured by the implantable medical device and/or through other suitable means. Data observations is data that crosses a parameter or metric threshold. The measured data observations are stored into the implantable medical device memory. The data is then subsequently transmitted and stored into the memory of the external device. Additionally, other data is transmitted and stored into memory which includes whether or not a patient experienced HFH during an evaluation period. Whether the HFH occurred at the beginning or the end of the evaluation period is irrelevant to predicting the prospective risk of HFH. The technique described herein merely determines that a HFH occurred sometime during the evaluation period.

After data is stored in the memory of the external device, the computer system defines a look back period as a set of evaluation time periods. For example, the look back period for a patient includes two consecutive evaluation periods—a preceding evaluation period and a current evaluation period. The preceding evaluation period occurs immediately before current evaluation period. In one or more embodiments, each evaluation period extends the same amount of time (e.g., 30 days, 45 days, 60 days, 75 days, 90 days etc.). In one or more other embodiments, evaluation periods may extend a different amount of time. For example, one evaluation period can be 30 days while another evaluation time period may be 35 days. In still yet another embodiment, the preceding evaluation period can encompass a substantially different amount of time than the current evaluation period (e.g. 90 days for the preceding evaluation period compared to 30 days for the current evaluation period). In one or more other embodiments, evaluation period could encompass the entire duration between two consecutive follow-up sessions. Alternatively, the entire duration could be variable for the same patient as time progresses. For example, entire duration between follow-up 1 and follow-up 2 could be 60 days and the duration between follow-up 2 and follow-up 3 could be 90 days.

Each evaluation period is categorized by its total amount of data observations experienced by that patient during that evaluation period. The total amount of data observations are counted without regard to the type of data observations. To categorize or classify the evaluation period, data observations are counted to determine the total amount of data observations that occurred during that evaluation period. For example, if 0 data observations exist during the evaluation period, the evaluation period is designated as 0 data observations and the evaluation period is placed into the 0 data observations category. A counter, associated with the zero data observations category, is then incremented by "1" to indicate that the evaluation period has been determined to have zero data observations. During or after categorizing all of the evaluation periods, each evaluation period or evaluation window, within a particular data observations category, is counted. After determining a total amount evaluations periods that were categorized as being within a data observations category (e.g. 0 data observations category, 1 data observations category, 2 data observations category, 3 data observations category etc.), the total amount is stored into the memory of the external device.

At the same time or about the same time, a determination is made as to whether a HFH had occurred for each current evaluation period experienced by a patient. If a HFH was experienced by a patient during the current evaluation period, a HFH counter for that particular data observations category is incremented by "1."

The risk of HFH is then estimated for each data observation category. For example, an equation for estimating HFH risk for each evaluation period, designated with 0, 1, 2, 3, or more data observations, is as follows:

The prospective risk of HFH is then estimated for each data observation category. For example, the equation for estimating HFH risk for each evaluation period, designated with 0, 1, 2, 3, or more data observations, is as follows:

$$\frac{\text{Number of Risk Prediction windows with} \geq 1 \ HFH}{\text{Total number of Risk Assessment windows}}$$

or, stated in another way, as follows:

HFH risk=(HFHnext)/Nnext where HFHnext is the total amount of HFH that occurred during the current prediction period (shown as "HFH" in FIG. 13B) for that particular data observations category while Nnext represents the total number of evaluation windows (also referred to as "risk assessment windows" or "risk prediction windows") that is associated with that particular data observations category.

Thereafter, a lookup table is created that associates total data observations during an evaluation period with prospective heart failure hospitalization. After the database has been completed and is stored in memory, a patient's prospective risk of heart failure hospitalization can be estimated using the lookup table.

For example, patient data can be acquired through an implantable medical device which indicates the patient experienced 2 data observations during a preceding evaluation period and 1 data observation for a current evaluation period. Using the total data observations, the lookup table is accessed and the heart failure hospitalization risk is determined for each evaluation period. In one or more embodiments, a prospective heart failure hospitalization risk is determined by using weighting factors in which the latter evaluation time period is weighted more heavily than an earlier evaluation time period. In one or more other embodiments, each evaluation period can be automatically weighted based upon user-defined input.

In one or more other embodiments, a physician is able to obtain a customized HFH risk for a patient by inputting data into the computer that requires a new lookup table to be generated that solely associates HFH patients' data with one or more characteristics of the physician's patient. For example, a new lookup table could be generated in which data is limited to heart failure data acquired from patients that have characteristics shared with the physician's patient such as gender (i.e. data limited to women alone, men alone), age (e.g. pediatric patients) or some other age grouping (i.e. over 40, over 50, over 60, 40 to 50, 50 to 60, 60 to 70, etc.) alone or other suitable categories. In one or more other embodiments, the HFH risk can be further customized by considering one or two parameters that may be more relevant to the patient's health history. For example, a physician may focus on a subset of parameters that are found in the database. A graphical user interface can then be used to display the patient's prospective heart failure hospitalization risk to the user.

The present disclosure is configured to provide a more realistic HFH risk than conventional methods. For example, in one or more embodiments, the prospective HFH risk is calculated by more heavily weighting the most recent evaluation period (i.e. current evaluation period) compared to the evaluation period preceding the current evaluation time period. Yet another distinction is that the present disclosure provides increased granular risk levels which also increases the accuracy of estimating risk of HFH. By being able to more realistically predict a patient's HFH risk using presently available diagnostic data, the patient or physician can act to minimize or potentially avoid a patient experiencing HFH. For example, therapy can be adjusted in order to avoid HFH. Preventing HFH can potentially improve long-term patient outcome while reducing costs of care.

The present disclosure achieves numerous benefits over conventional methods. For example, skilled artisans will appreciate that the present disclosure is able to present increased gradations of HFH risk instead of broad risk categories. Additionally, compared to conventional methods, the present disclosure easily estimates prospective risk of HFH without unduly burdening healthcare providers by merely requiring a total count of data observations within an evaluation period.

FIG. 1 is a conceptual drawing illustrating an example system 10 configured to transmit diagnostic information indicative of heart failure of patient 14. In the example of FIG. 1, system 10 includes IMD 16, which is coupled to leads 18, 20, and 22 and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

In general, the techniques described in this disclosure may be implemented by any medical device, e.g., implantable or external, that senses a signal indicative of cardiac activity, patient 14 activity, and/or fluid volume within patient 14. As one alternative example, the techniques described herein may be implemented in an external cardiac monitor that generates electrograms of heart 12 and detects thoracic fluid volumes, respiration, and/or cardiovascular pressure of patient 14.

In the example of FIG. 1, leads 18, 20, 22 extend into the heart 12 of patient 14 to sense electrical activity of heart 12 and/or deliver electrical stimulation to heart 12. Leads 18, 20, and 22 may also be used to detect a thoracic impedance indicative of fluid volume in patient 14, respiration rates, sleep apnea, or other patient metrics. Respiration metrics, e.g., respiration rates, tidal volume, and sleep apnea, may also be detectable via an electrogram, e.g., based on a signal component in a cardiac electrogram that is associated with respiration. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava, or other veins. Furthermore, in some examples, system 10 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to detect intrathoracic impedance as a patient metric for identifying a heart failure risk or fluid retention levels.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for patient metrics stored in IMD 16 and/or used in generating the heart failure risk level. IMD 16 may utilize two of any electrodes carried on leads 18, 20, 22 to generate electrograms of cardiac activity. In some examples, IMD 16 may also use a housing electrode of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor heart rate (night time and day time), heart rate variability, ventricular or atrial intrinsic pacing rates, indicators of blood flow, or other indicators of the ability of heart 12 to pump blood or the progression of heart failure.

In some examples, IMD 16 may also use any two electrodes of leads 18, 20, and 22 or the housing electrode to sense the intrathoracic impedance of patient 14. As the tissues within the thoracic cavity of patient 14 increase in fluid content, the impedance between two electrodes may also change. For example, the impedance between an RV coil electrode and the housing electrode may be used to monitor changing intrathoracic impedance.

IMD 16 may use intrathoracic impedance to create a fluid index. As the fluid index increases, more fluid is being retained within patient 14 and heart 12 may be stressed to keep up with moving the greater amount of fluid. Therefore, this fluid index may be a patient metric transmitted in diagnostic data or used to generate the heart failure risk level. By monitoring the fluid index in addition to other patient metrics, IMD 16 may be able to reduce the number of false positive heart failure identifications relative to what might occur when monitoring only one or two patient metrics. Furthermore, IMD 16, along with other networked computing devices described herein, may facilitate remote monitoring of patient 14, e.g., monitoring by a health care professional when the patient is not located in a healthcare facility or clinic associated with the health care professional, during a post-hospitalization period. An example system for measuring thoracic impedance and determining a fluid index is described in U.S. Patent Publication No. 2010/0030292 to Sarkar et al., entitled, "DETECTING WORSENING HEART FAILURE BASED ON IMPEDANCE MEASUREMENTS," which published on Feb. 4, 2010 and is incorporated herein by reference in its entirety.

IMD 16 may also communicate with external programmer 24. In some examples, programmer 24 comprises an external device, e.g., a handheld computing device, computer workstation, or networked computing device. Programmer 24 may include a user interface that receives input from a user. In other examples, the user may also interact with programmer 24 remotely via a networked computing device. The user may interact with programmer 24 to communicate with IMD 16. For example, the user may interact with programmer 24 to send an interrogation request and retrieve patient metrics or other diagnostic information from IMD 16. A user may also interact with programmer 24 to program IMD 16, e.g., select values for operational parameters of IMD 16. Although the user is a physician, technician, surgeon, electrophysiologist, or other healthcare professional, the user may be patient 14 in some examples.

For example, the user may use programmer 24 to retrieve information from IMD 16 regarding patient metric data and/or the heart failure risk level. Heart failure risk level may be transmitted as diagnostic information. Although programmer 24 may retrieve this information after submitting an interrogation request, IMD 16 may push or transmit the heart failure risk level, for example, if the heart failure risk level indicates a change in patient treatment is necessary. For example, gradations of risk level may be determined based on a total number of times that patient metrics exceed their representative thresholds. Additionally or alternatively, the risk level may be solely determined by total number of data observations associated with one or more metrics over a pre- or post-specified time period.

IMD 16, external device 114, and/or programmer 24 may generate the HFH risk level. Exemplary patient metric data may include intracardiac or intravascular pressure, activity, posture, respiration, thoracic impedance, impedance trend etc.

As another example, the user may use programmer 24 to retrieve information from IMD 16 regarding the performance or integrity of IMD 16 or other components of system 10, such as leads 18, 20 and 22, or a power source of IMD 16. In some examples, any of this information may be presented to the user as an alert (e.g., a notification or instruction). Further, alerts may be pushed from IMD 16 to facilitate alert delivery whenever programmer 24 is detectable by IMD 16. IMD 16 may wirelessly transmit alerts, or other diagnostic information, to facilitate immediate notification of the heart failure condition.

Programmer 24 may also allow the user to define how IMD 16 senses, detects, and manages each of the patient metrics. For example, the user may define the frequency of sampling or the evaluation window used to monitor the patient metrics. Additionally or alternatively, the user may use programmer 24 to set each metric threshold used to monitor the status of each patient metric. The metric thresholds may be used to determine when one or more patient metrics has reached a magnitude indicative of being at risk for heart failure and/or heart failure hospitalization. In some examples, when a data exceeds its respective metric threshold, the metric may be counted for that evaluation period. For example, if one or more patient metrics exceed their thresholds a predetermined number of times, the HFH risk level may be shown in gradations of increased risk level for patient 14 to be hospitalized, e.g. within thirty days. The HFH risk level is based upon a predetermined number of data observations. In other examples, the predetermined number may be set to a different number or a risk level percentage (fraction). In this manner, the predetermined number is exceeded metrics thresholds. Programmer 24 may be used to set this predetermined number or any other factors used to generate and interpret the heart failure risk level.

IMD 16 and programmer 24 may communicate via wireless communication using any techniques known in the art. Examples of communication techniques may include, for example, radiofrequency (RF) telemetry, but other communication techniques such as magnetic coupling are also contemplated. In some examples, programmer 24 may include a programming head that may be placed proximate to the body of the patient near the IMD 16 implant site in order to improve the quality or security of communication between IMD 16 and programmer 24.

IMD 16 may automatically detect each of the patient metrics and store them within the IMD for later transmission. Although IMD 16 may automatically detect a number (e.g. 10 or less) different patient metrics in some examples, IMD 16 may detect more or less patient metrics in other examples. For example, the patient metrics may include two or more of a thoracic fluid index, an atrial fibrillation duration, a ventricular contraction rate during atrial fibrillation, a patient activity, a nighttime heart rate, a heart rate variability, a cardiac resynchronization therapy (CRT) percentage (e.g., the percentage of cardiac cycles for which cardiac resynchronization pacing was provided), or the occurrence of or number of therapeutic electrical shocks. The metric-specific thresholds may include at least two of a thoracic fluid index threshold of approximately 60, an atrial fibrillation duration threshold of approximately 6 hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, or an electrical shock threshold of 1 electrical shock. In addition to transmitting diagnostic information during a hospitalization period and a post-hospitalization period, IMD 16 may transmit diagnostic information to a clinician or other user prior to the hospitalization period. In other words, IMD 16 may transmit a heart failure risk level to a clinician before patient 14 is ever admitted to the hospital for a heart failure decompensation event. The risk level transmitted may be similar to the post-hospitalization risk level, but, in some examples, the risk level transmitted prior to hospitalization may be transmitted less frequently, in response to an interrogation request from the clinician or other user, or upon the risk level reaching a more severe level, e.g., a high or medium risk of hospitalization.

In addition, IMD 16 may alter the method with which patient metrics are stored within IMD 16. In other words, IMD 16 may store the automatically detected data observations with a dynamic data storage rate. Before patient 14 is admitted to the hospital, e.g., before the hospitalization period, the clinician or admitting healthcare professional may submit an interrogation request to IMD 16 in order to retrieve a portion of the stored patient metrics. The patient metrics may help the clinician determine if hospitalization of patient 14 is a prudent action for treatment. In response to the interrogation request, IMD 16 may transmit at least some of the automatically detected patient metrics stored in IMD 16.

Figure 2A:
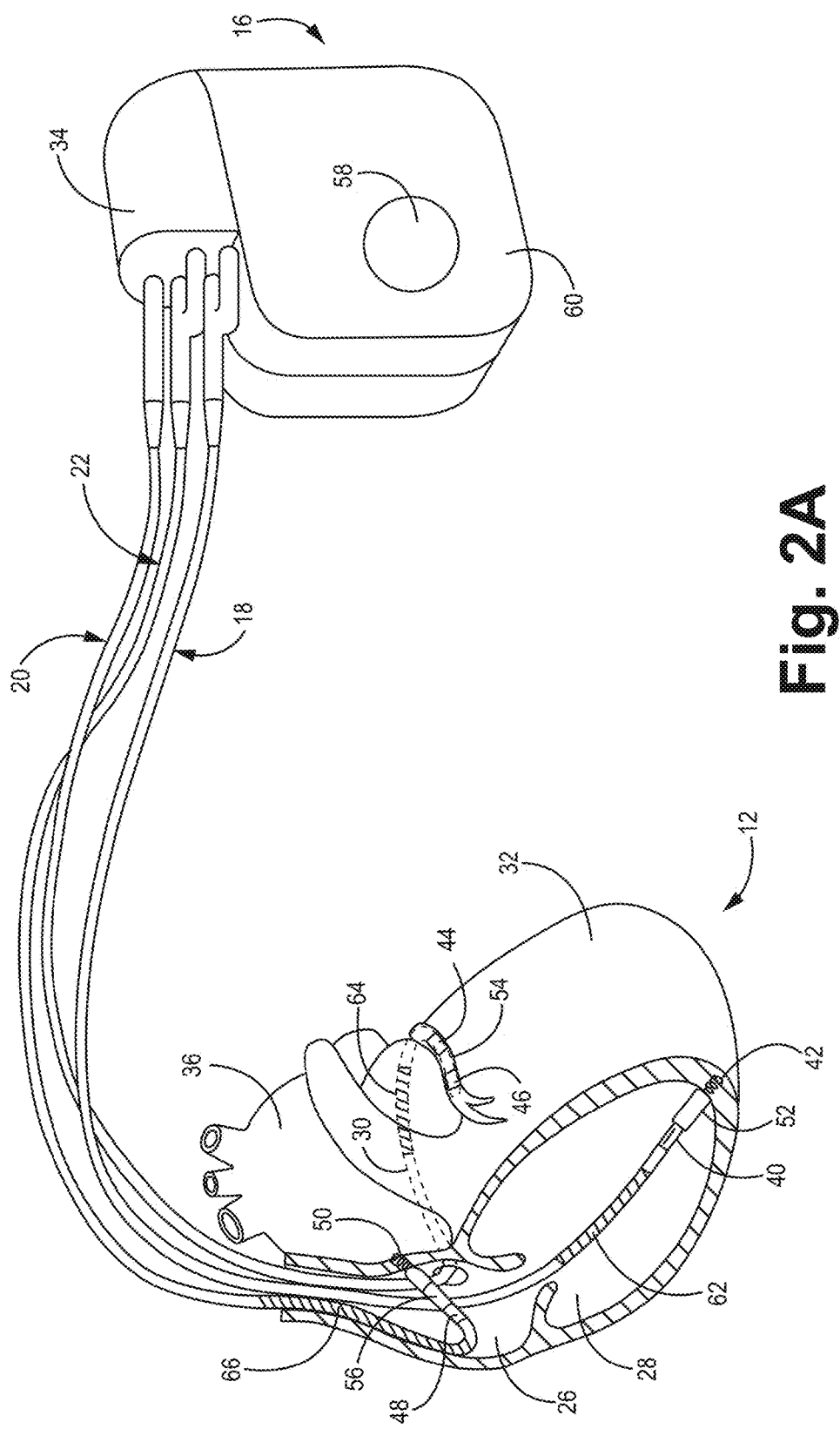
FIG. 2A is a conceptual drawing illustrating the example IMD and leads of FIG. 1 in conjunction with a heart.

FIG. 2A is a conceptual drawing illustrating IMD 16 and leads 18, 20, and 22 of system 10 in greater detail. As shown in FIG. 2A, IMD 16 is coupled to leads 18, 20, and 22. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16, or otherwise coupled to housing 60. In some examples, housing electrode 58 is defined by an uninsulated portion of an outward facing portion of housing 60 of IMD 16. Other division between insulated and uninsulated portions of housing 60 may be employed 1*i* to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or subcutaneous electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may sense electrical signals and/or deliver defibrillation pulses and other therapies to heart 12 via percutaneous leads that extend through the skin of patient 14 to a variety of positions within or outside of heart 12. Further, external electrodes or other sensors may be used by IMD 16 to deliver therapy to patient 14 and/or sense and detect patient metrics used to generate diagnostic information, e.g., a heart failure risk level.

Figure 2B:
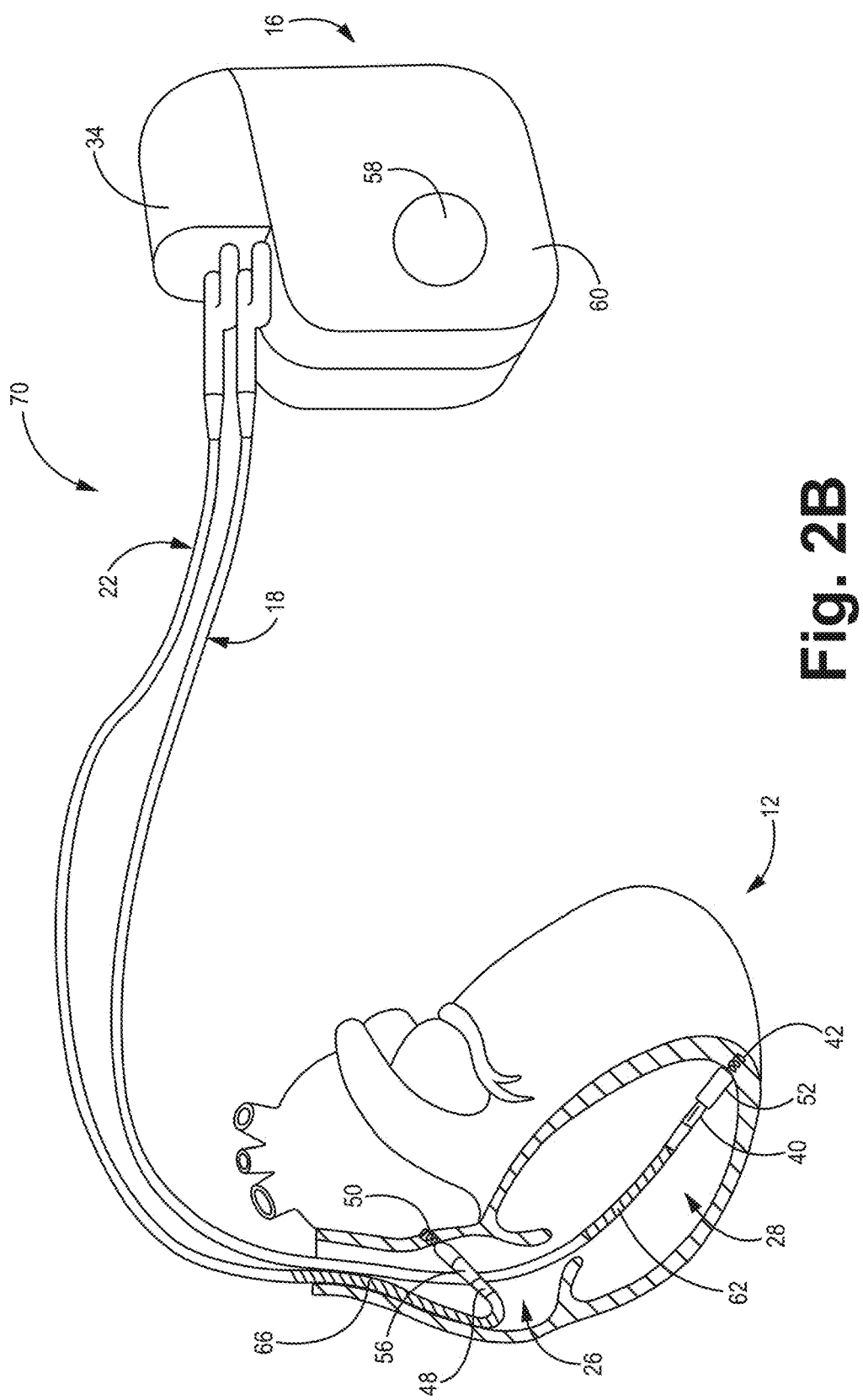
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, systems in accordance with this disclosure may include three transvenous leads located as illustrated in FIGS. 1 and 2, and an additional lead located within or proximate to left atrium 36. As another example, systems may include a single lead that extends from IMD 16 into right atrium 26 or right ventricle 28, or two leads that extend into a respective one of the right ventricle 26 and right atrium 26. An example of a two lead type of system is shown in FIG. 2B. Any electrodes located on these additional leads may be used in sensing and/or stimulation configurations.

Any of electrodes 40, 42, 44, 46, 48, 50, 62, 64, 66, and 58 may be utilized by IMD 16 to sense or detect patient metrics used to generate the heart failure risk level for patient 14. Typically, IMD 16 may detect and collect patient metrics from those electrode vectors used to treat patient 14. For example, IMD 16 may derive an atrial fibrillation duration, heart rate, and heart rate variability metrics from electrograms generated to deliver pacing therapy. However, IMD 16 may utilize other electrodes to detect these types of metrics from patient 14 when other electrical signals may be more appropriate for therapy.

In addition to electrograms of cardiac signals, any of electrodes 40, 42, 44, 46, 48, 50, 62, 64, 66, and 58 may be used to sense non-cardiac signals. For example, two or more electrodes may be used to measure an impedance within the thoracic cavity of patient 14. Intrathoracic impedance may be used to generate a fluid index patient metric that indicates the amount of fluid building up within patient 14. Since a greater amount of fluid may indicate increased pumping loads on heart 12, the fluid index may be used as an indicator of HFH risk. IMD 16 may periodically measure the intrathoracic impedance to identify a trend in the fluid index over days, weeks, months, and even years of patient monitoring. In general, the two electrodes used to measure the intrathoracic impedance may be located at two different positions within the chest of patient 14. For example, coil electrode 62 and housing electrode 58 may be used as the sensing vector for intrathoracic impedance because electrode 62 is located within RV 28 and housing electrode 58 is located at the IMD 16 implant site generally in the upper chest region. However, other electrodes spanning multiple organs or tissues of patient 14 may also be used, e.g., an additional implanted electrode used only for measuring thoracic impedance.

FIG. 2B is a conceptual diagram illustrating another example system 70, which is similar to system 10 of FIGS. 1 and 2A, but includes two leads 18, 22, rather than three leads. Leads 18, 22 are implanted within right ventricle 28 and right atrium 26, respectively. System 70 shown in FIG. 2B may be useful for physiological sensing and/or providing pacing, cardioversion, or other therapies to heart 12. Detection of patient diagnostic data according to this disclosure may be performed in two lead systems in the manner described herein with respect to three lead systems. In other examples, a system similar to systems 10 and 70 may only include one lead (e.g., any of leads 18, 20 or 22) to deliver therapy and/or sensor and detect patient metrics related to monitoring risk of heart failure. Alternatively, diagnostic data may be implemented in systems utilizing subcutaneous leads, subcutaneous IMDs, or even external medical devices. Although FIGS. 1-2 provide some useful IMD 16 implantation examples, skilled artisans appreciate that IMD 16 and its associated electrodes can be implanted in other locations of the body and can include leads or be leadless.

Figure 3:
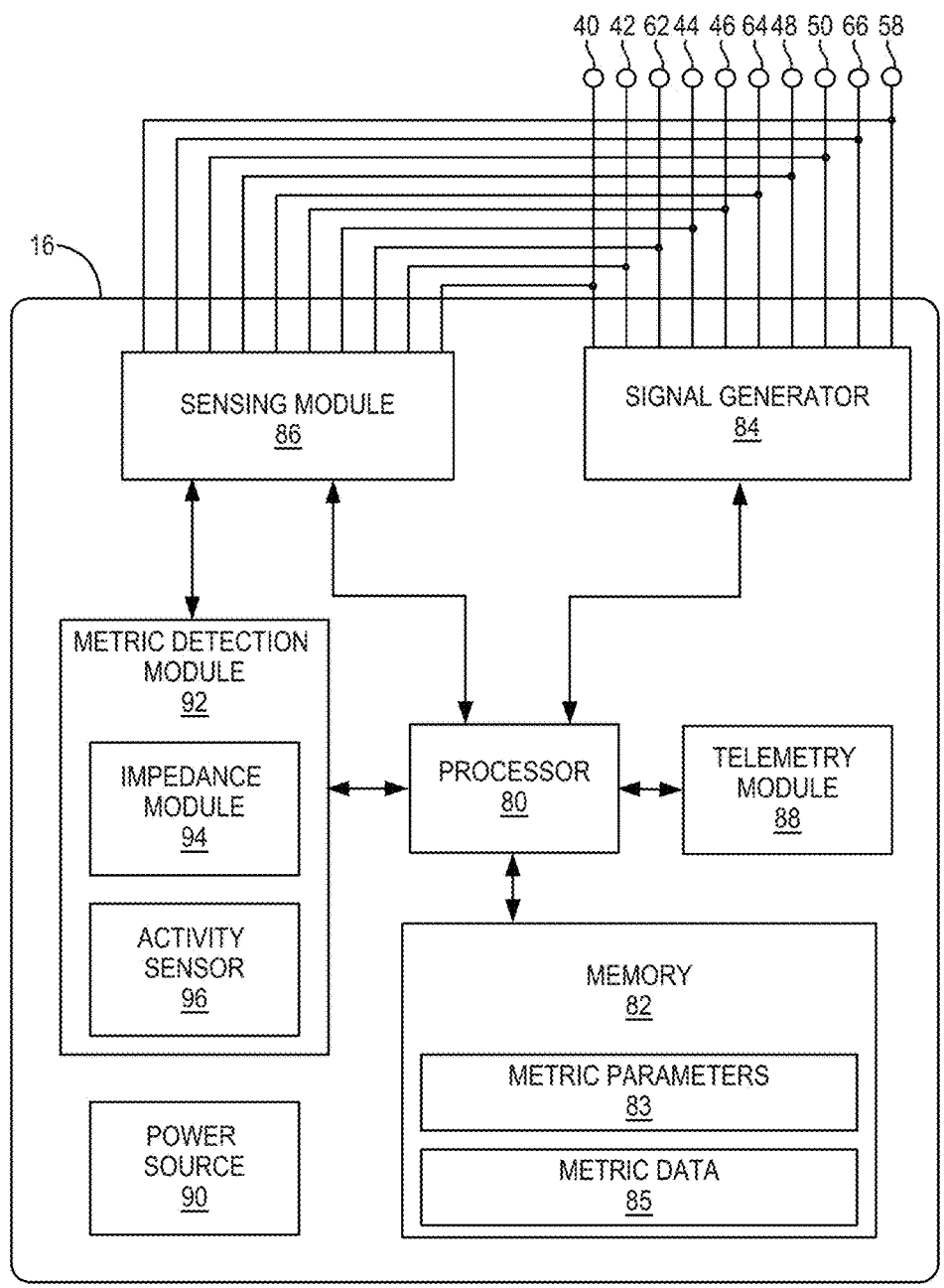
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, metric detection module 92, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a therapy parameters, which may be stored in memory 82. For example, processor 80 may control signal generator 84 to deliver electrical pulses with the amplitudes, pulse widths, frequency, or electrode polarities specified by the therapy parameters.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon. Sensing may be done to determine heart rates or heart rate variability, or to detect arrhythmias or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR, CRT, and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. Processor 80 detects data (e.g. data observations etc.) at an IMD16 check and/or interrogation time point. Data is sensed based on signals from sensing module 86. Additionally, cardioversion or defibrillation shock can be determined to be needed based upon sensed data, and processor 80 may control the amplitude, form and timing of the shock delivered by signal generator 84.

Memory 82 is configured to store data. Exemplary data can be associated with a variety of operational parameters, therapy parameters, sensed and detected data, and any other information related to the therapy and treatment of patient 14. In the example of FIG. 3, memory 82 also includes metric parameters 83 and metric data 85. Metric parameters 83 may include all of the parameters and instructions required by processor 80 and metric detection module 92 to sense and detect each of the patient metrics used to generate the diagnostic information transmitted by IMD 16. Metric data 85 may store all of the data generated from the sensing and detecting of each patient metric. In this manner, memory 82 stores a plurality of automatically detected patient metrics as the data required to generate a risk level of patient 14 being admitted to the hospital due to heart failure.

Metric parameters 83 may include definitions of each of the patient metrics automatically sensed or measured by metric detection module 92. These definitions may include instructions regarding what electrodes or sensors to use in the detection of each metric. Preferred metrics include an (1) impedance trend index (also referred to as OPTIVOL® commercially available in IMDs from Medtronic Inc., located in MN), (2) intrathoracic impedance, (3) atrial tachycardia/atrial fibrillation (AT/AF) burden, (4) mean ventricular rate during AT/AF, (5) patient activity, (6) V rate, (7) day and night heart rate, (8) percent CRT pacing, and/or (9) number of shocks. OPTIVOL® is described with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein. Other suitable metrics can also be used. For example, a reference or baseline level impedance is established for a patient from which subsequently acquired raw impedance data is compared. For example, raw impedance can be acquired from the electrodes (e.g. RV coil to Can) and compared to the reference impedance. Baseline impedance can be derived by averaging impedance over a duration of 7 (1-week) days to 90 days (3-months).

Metric parameters 83 may also store a metric-specific threshold for each of the patient metrics automatically detected by metric detection module 92. Metric thresholds may be predetermined and held constant over the entire monitoring of patient 14. In some examples, however, metric thresholds may be modified by a user during therapy or processor 80 may automatically modify one or more metric thresholds to compensate for certain patient conditions. For example, a heart rate threshold may be changed over the course of monitoring if the normal or baseline heart rate has changed during therapy.

In one example, these metric-specific thresholds may include a thoracic fluid index threshold of approximately 60, an atrial fibrillation burden threshold of approximately 6 consecutive hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock number threshold of 1 electrical shock. These thresholds may be different in other examples, and may be configured by a user, e.g., a clinician, for an individual patient.

Processor 80 may alter the method with which patient metrics are stored in memory 82 as metric data 85. In other words, processor 80 may store the automatically detected patient metrics with a dynamic data storage rate. Metric detection module 92 may, for example, transmit diagnostic data that is based on the patient metrics and whether any of the metrics exceed the respective specific metric thresholds. Any time that an automatically detected patient metric exceeds their respective metric threshold, the patient metric can be counted.

In this manner, metric detection module 92 may automatically detect each of the patient metrics and store them within metric data 85 for later transmission.

Example fluid index values and impedance measurements are described in U.S. Patent Application No. 2010/0030292 entitled "DETECTING WORSENING HEART FAILURE BASED ON IMPEDANCE MEASUREMENTS," which is incorporated by reference herein in its entirety. As the intrathoracic impedance remains low, the fluid index may increase. Conversely, as the intrathoracic impedance remains high, the fluid index may decrease. In this manner, the fluid index value maybe a numerical representation of retained fluid that is specific to patient 14. In other examples, the intrathoracic impedance may be alternatively used.

Metric data 85 is a portion of memory 82 that may store some or all of the patient metric data that is sensed and/or detected by metric detection module 92. Metric data 85 may store the data for each metric on a rolling basis during an evaluation window. The evaluation window may only retain recent data and delete older data from the evaluation window when new data enters the evaluation window. In this manner, the evaluation window may include only recent data for a predetermined period of time. In one or more other embodiments, memory can be configured for long term storage of data. Processor 80 may access metric data when necessary to retrieve and transmit patient metric data and/or generate heart failure risk levels. In addition, metric data 85 may store any and all data observations, heart failure risk levels or other generated information related to the heart failure risk of patient 14. The data stored in metric data 85 may be transmitted as part of diagnostic information. Although metric parameters 83 and/or metric data 85 may consist of separate physical memories, these components may simply be an allocated portion of the greater memory 82.

Metric detection module 92 may automatically sense and detect each of the patient metrics. Metric detection module 92 may then generate diagnostic data, e.g., data that indicates a threshold has been crossed, risk levels, based on the patient metrics. For example, metric detection module 92 may measure the thoracic impedance, analyze an electrogram of heart 12, monitor the electrical stimulation therapy delivered to patient 14, or sense the patient activity. It is noted that functions attributed to metric detection module 92 herein may be embodied as software, firmware, hardware or any combination thereof. In some examples, metric detection module 92 may at least partially be a software process executed by processor 80. Metric detection module 92 may sense or detect any of the patient metrics used as a basis for generating the heart failure risk level or otherwise indication of heart failure status or that patient 14 is at risk for hospitalization. In one example, metric detection module 92 may compare each of the patient metrics to their respective metric-specific thresholds defined in metric parameters 83 to generate the heart failure risk level. Metric detection module 92 may automatically detect two or more patient metrics. In other examples, metric detection module 92 may detect different patient metrics.

In one example, metric detection module 92 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Metric detection module 92 may also analyze electrograms in conjunction with a real-time clock, patient posture or activity signal, e.g., from activity sensor 96, and/or other physiological signals indicative of when a patient is asleep or awake to determine a nighttime (or sleeping) heart rate or a daytime (or awake) heart rate or a difference between the day and night heart rate, and also analyze electrograms to determine a heart rate variability, or any other detectable cardiac events from one or more electrograms. As described above, metric detection module 92 may use peak detection, interval detection, or other methods to analyze the electrograms.

In addition, metric detection module 92 may include and/or control impedance module 94 and activity sensor 96. Impedance module 94 may be used to detect the thoracic impedance used to generate the thoracic fluid index. As described herein, impedance module 94 may utilize any of the electrodes of FIG. 1, 2 or 3 to take intrathoracic impedance measurements. In other examples, impedance module 94 may utilize separate electrodes coupled to IMD 16 or in wireless communication with telemetry module 88. Once impedance module 94 measures the intrathoracic impedance of patient 14, metric detection module 92 may generate the thoracic fluid index and compare the index to the thoracic fluid index threshold defined in metric parameters 83.

Activity sensor 96 may include one or more accelerometers or other devices capable of detecting motion and/or position of patient 14. Activity sensor 96 may therefore detect activities of patient 14 or postures engaged by patient 14. Metric detection module 92 may, for example, monitor the patient activity metric based on the magnitude or duration of each activity and compare the determined metric data to the activity threshold defined in metric parameters 83. In addition to detecting events of patient 14, metric detection module 92 may also detect certain therapies delivered by signal generator 84, e.g., as directed by processor 80. Metric detection module 92 may monitor signals through signal generator 84 or receive therapy information directly from processor 80 for the detection. Example patient metrics detected by this method may include a cardiac resynchronization therapy percentage or metrics related to delivery of electrical shocks.

The cardiac resynchronization therapy (CRT) metric may be the amount or percentage of time each day, or an amount of percentage of cardiac cycles, as examples, that IMD 16 delivers cardiac resynchronization therapy to heart 12. Low CRT amounts or percentages may indicate that beneficial therapy is not being effectively delivered and that adjustment of therapy parameters, e.g., an atrioventricular delay or a lower pacing rate, may improve therapy efficacy. In one example, higher CRT amounts or percentages may indicate that heart 12 is sufficiently pumping blood through the vasculature with the aid of therapy to prevent fluid buildup. In examples of other types of cardiac pacing (non-CRT) or stimulation therapy, higher therapy percentages may indicate that heart 12 is unable to keep up with blood flow requirements.

An electrical shock may be a defibrillation event or other high energy shock used to return heart 12 to a normal rhythm. The metric related electrical shocks may be a number or frequency of electrical shocks, e.g., a number of shocks within a period of time. Metric detection module 92 may detect these patient metrics as well and compare them to a cardiac resynchronization therapy percentage and shock event threshold, respectively, defined in metric parameters 83 to determine when each patient metric has become critical. In one example, the electrical shock event metric may become critical when a threshold number of shocks is delivered, e.g., within a time period, or even when patient 14 even receives one therapeutic shock.

Metric detection module 92 may include additional sub-modules or sub-routines that detect and monitor other patient metrics used to monitor patient 14 and/or generate the HFH risk level. In some examples, metric detection module 92, or portions thereof, may be incorporated into processor 80 or sensing module 86. In other examples, raw data used to produce patient metric data may be stored in metric data 85 for later processing or transmission to an external device. An external device may then produce each patient metric from the raw data, e.g., electrogram or intrathoracic impedance. In other examples, metric detection module 92 may additionally receive data from one or more implanted or external devices used to detect each metric which IMD 16 may store as metric data.

In some examples, the patient metric thresholds used to generate the risk levels may change over time, e.g., the patient metric thresholds may either be modified by a user or automatically changed based on other patient conditions. Telemetry module 88 may receive commands from programmer 24, for example, to modify one or more metric parameters 83 (e.g., metric creation instructions or metric-specific thresholds). In some examples, processor 80 may automatically adjust a metric-specific threshold if certain conditions are present in patient 14. For example, the threshold may be adjusted if patient 14 is experiencing certain arrhythmias or data contained in cardiac electrograms change, e.g., there is a deviation in ST elevations or presence of pre-ventricular contractions, in such a manner that requires a change in the threshold.

Processor 80 may generate the HFH risk level based upon the patient metrics sensed, detected, and stored in metric data 85 of memory 82. For example, processor 80 may continually update the HFH risk level as metric detection module 92 updates each patient metric. In other examples, processor 80 may periodically update the HFH risk level according to an updating schedule. In one or more other embodiments, the total number of data observations that exceed a threshold within a pre-specified period of time can be used to determine the risk of heart failure hospitalization.

As described above, processor 80 may provide an alert to a user, e.g., of programmer 24, regarding the data from any patient metric and/or the HFH risk level.

In one example, processor 80 may provide an alert with the HFH risk level when programmer 24 or another device communicates with IMD 16. Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., patient metric data. In other examples, one or more steps in the generation of the heart failure risk level may occur within a device external of patient 14, e.g., within programmer 24 or a server networked to programmer 24. In this manner, IMD 16 may detect and store patient metrics before transmitting the patient metrics to a different computing device.

In addition to transmitting diagnostic information during a hospitalization period and a post-hospitalization period, processor 80 may control telemetry module 88 to transmit diagnostic information to a clinician or other user prior to the hospitalization period. If one of the automatically detected patient metrics exceeds its respective metric-specific threshold, processor 80 may control telemetry module to transmit that patient metric and possibly other patient metrics to allow the clinician to more accurately diagnose the problem with patient 14.

Figure 4:
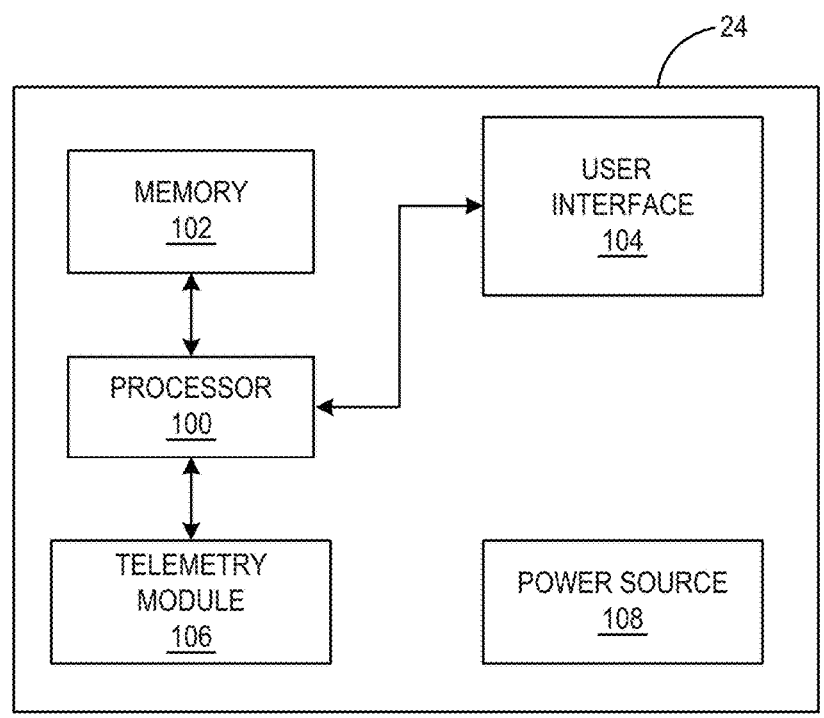
FIG. 4 is a functional block diagram illustrating an example configuration of an external programmer that facilitates user communication with the IMD.

FIG. 4 is a functional block diagram illustrating an example configuration of external programmer 24. As shown in FIG. 4, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to configure the operational parameters of and retrieve data from IMD 16 (FIG. 1). The clinician may interact with programmer 24 via user interface 104, which may include display to present graphical user interface to a user, and a keypad or another mechanism for receiving input from a user. In addition, the user may receive an alert or notification from IMD 16 indicating the heart failure risk level and/or patient metrics via programmer 24. In other words, programmer 24 may receive diagnostic information from IMD 16.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, telemetry module 106 may transmit an interrogation request to telemetry module 88 of IMD 16. Accordingly, telemetry module 106 may receive data (e.g. diagnostic information etc.) or diagnostic information selected by the request or based on already entered patient status to IMD 16. The data may include patient metric values or other detailed information from telemetry module 88 of IMD 16. The data may include an alert or notification of the heart failure risk level from telemetry module 88 of IMD 16. The alert may be automatically transmitted, or pushed, by IMD 16 when the heart failure risk level becomes critical. In addition, the alert may be a notification to a healthcare professional, e.g., a clinician or nurse, of the risk level and/or an instruction to patient 14 to seek medical treatment for the potential heart failure condition that may require re-hospitalization is left untreated. In response to receiving the alert, user interface 104 may present the alert to the healthcare professional regarding the risk level or present an instruction to patient 14 to seek medical treatment.

Either in response to heart failure data, e.g., the risk level or patient metrics, or requested heart failure information, user interface 104 may present the patient metrics and/or the heart failure risk level to the user. In some examples, user interface 104 may also highlight each of the patient metrics that have exceeded the respective one of the plurality of metric-specific thresholds. In this manner, the user may quickly review those patient metrics that have contributed to the identified heart failure risk level.

Upon receiving the alert via user interface 104, the user may also interact with user interface 104 to cancel the alert, forward the alert, retrieve data regarding the heart failure risk level (e.g., patient metric data), modify the metric-specific thresholds used to determine the risk level, or conduct any other action related to the treatment of patient 14. In some examples, the clinician may be able to review raw data to diagnose any other problems with patient 14 or monitor the efficacy of treatments given to patient 14. For example, the clinician may check if the intrathoracic impedance has increased after diuretic therapy or if the heart rate has decreased during atrial fibrillation in response to a rate controlling drug. User interface 104 may even suggest treatment along with the alert, e.g., certain drugs and doses, to minimize symptoms and tissue damage that could result from heart failure. User interface 104 may also allow the user to specify the type and timing of alerts based upon the severity or criticality of the heart failure risk level. In addition to the heart failure risk level, in other examples, user interface 104 may also provide the underlying patient metrics to allow the clinician to monitor therapy efficacy and remaining patient conditions.

In some examples, processor 100 of programmer 24 and/or one or more processors of one or more networked computers may perform all or a portion of the techniques described herein with respect to processor 80, metric detection module 92 and IMD 16. For example, processor 100 or a metric detection module 92 within programmer 24 may analyze patient metrics to detect those metrics exceeding thresholds and to generate the heart failure risk level.

Figure 5:
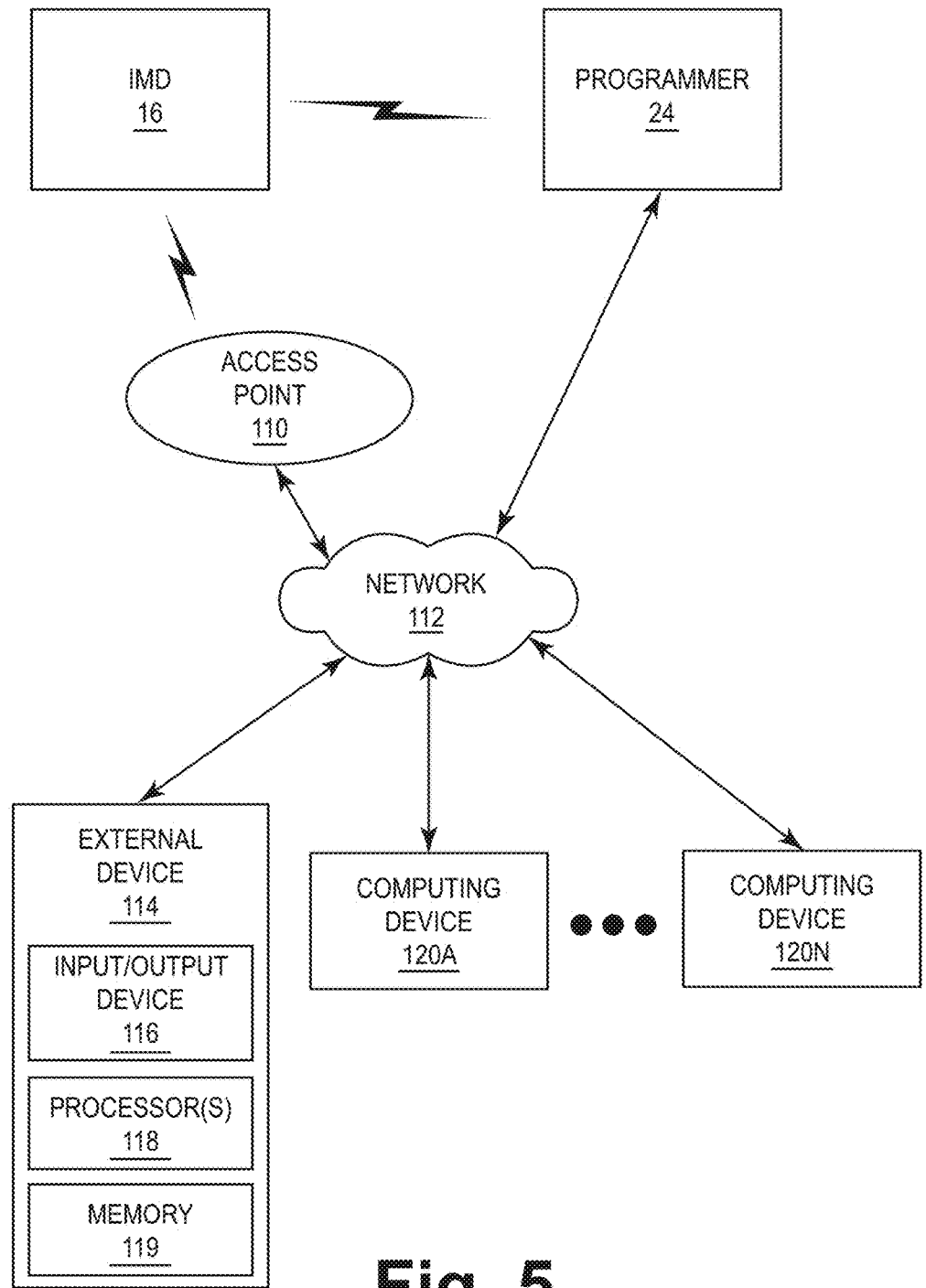
FIG. 5 is a block diagram illustrating an example computer system that includes an external device and one or more computing devices that are coupled to the IMD and programmer shown in FIG. 1 via a network.

FIG. 5 is a block diagram illustrating an example system that includes an external device 114 (e.g. server, etc.), and one or more computing devices 120A-120N, that are coupled to the IMD 16 and programmer 24 shown in FIG. 1 via a network 112. Network 112 may be generally used to transmit diagnostic information (e.g., a risk level) from a remote IMD 16 to another external computing device during a post-hospitalization period. However, network 112 may also be used to transmit diagnostic information from IMD 16 to an external computing device within the hospital so that a clinician or other healthcare professional may monitor patient 14. In this example, IMD 16 may use its telemetry module 88 to communicate with programmer 24 via a first wireless connection, and to communication with an access point 110 via a second wireless connection. In the example of FIG. 5, access point 110, programmer 24, external device 114, and computing devices 120A-120N are interconnected, and able to communicate with each other, through network 112. In some cases, one or more of access point 110, programmer 24, external device 114, and computing devices 120A-120N may be coupled to network 112 through one or more wireless connections. IMD 16, programmer 24, external device 114, and computing devices 120A-120N may each comprise one or more processors, such as one or more microprocessors, DSPs, ASICs, FPGAs, programmable logic circuitry, or the like, that may perform various functions and operations, such as those described herein. Access point 110 may comprise a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein. For example, access point 110 may include a home-monitoring unit that is co-located with patient 14 and that may monitor the activity of IMD 16. In some examples, external device 114 or computing devices 120 may control or perform any of the various functions or operations described herein, e.g., generate a heart failure risk level based on the patient metric comparisons or create patient metrics from the raw metric data. External device 114 further includes input/output device 116, processor 118 and memory 119. Input/output device 116 includes input devices such as a keyboard, a mouse, voice input etc. and output device includes graphical user interfaces, printers and other suitable means. Processor 118 includes any suitable processor such as Intel Xeon Phi. Processor 118 is configured to set the start and end dates for each evaluation period. The evaluation period serves as an evaluation window that encompasses data, acquired from each patient, that are within the boundaries (i.e. start and end times). Processor 118 is also configured to perform a variety of calculations. For example, processor 118 calculates risk of HFH for each evaluation period. In one or more embodiments, weighting factors are applied to two or more evaluations periods to determine the Frisk.

Memory 119 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Memory 119 stores data. Exemplary data stored in memory 119 includes heart failure patient data, heart failure prospective risk data etc. Evaluation period start and end times are also stored in memory. Heart failure patient data includes data observations (e.g. data sensed from sensors that cross a threshold). Additionally, evaluation period data is also stored in memory 119. For example, the start and end dates of the evaluation period data is stored in memory 119.

In some cases, external device 114 may be configured to provide a secure storage site for archival of diagnostic information (e.g., patient metric data and/or heart failure risk levels) that has been collected and generated from IMD 16 and/or programmer 24. Network 112 may comprise a local area network, wide area network, or global network, such as the Internet. In some cases, programmer 24 or external device 114 may assemble the diagnostic data, heart failure data, prospective heart failure risk data or other suitable data in web pages or other documents for viewing by and trained professionals, such as clinicians, via viewing terminals associated with computing devices 120. The system of FIG. 5 may be implemented, in some aspects, with general network technology and functionality similar to that provided by the Medtronic CareLink® Network developed by Medtronic, Inc., of Minneapolis, Minn.

In the manner of FIG. 5, computing device 120A or programmer 24, for example, may be remote computing devices that receive and present diagnostic information transmitted from IMDs of multiple patients so that a clinician may prioritize the patients needing treatment immediately. In other words, the clinician may triage patients by analyzing the HFH levels of multiple patients. The computing device may use its communication module to receive the diagnostic information (e.g., heart failure data) transmitted from multiple IMDs via network 112.

FIG. 6 illustrates an exemplary screen 130 of user interface 104 that includes diagnostic data. As shown in FIG. 6, screen 130 includes risk level 144 that indicates the risk that patient 14 will be hospitalized due to heart failure. As described herein, the heart failure risk level may be indicative that patient 14 would be hospitalized for a first time or hospitalized for another time (e.g., re-hospitalized or re-admitted). Although screen 130 is described as being presented on user interface 104 of programmer 24, screen 130 may be presented on any user interface of any device used by a healthcare professional. The heart failure report of screen 130 may be transmitted to a user at a scheduled frequency, e.g., once a day or once a week, or in response to an interrogation request from the user. As shown in FIG. 6, screen 130 is a heart failure report that includes identification data 132 and patient history data 134. Identification data 132 includes items such as the patient name, the device name, the serial number of IMD 16, the date, and even the physician name. Patient history data 134 may be relevant data that may help in the treatment of patient 14.

Screen 130 also includes clinical status 136 that includes information regarding the stimulation therapy delivered by IMD 16. Screen 130 also presents trend summary 138. Trend summary 138 presents a snapshot of certain patient metrics that are exceeding their respective metric thresholds to contribute to the severity of risk level 144. Critical indicator 140 is provided to remind the user that each of the patient metrics with critical indicator 140 is contributing to the risk level because the metric threshold has been met or exceeded. In examples in which risk level 144 is determined with a statistical analysis, critical indicator 140 may not be necessary. However, certain patient metrics that contribute significantly to the probability that patient 14 may be re-hospitalized may still be presented to the user.

In the example of FIG. 6, trend summary 138 presents four patient metrics 142A, 142B, 142C, and 142D (collectively "patient metrics 142"). Thoracic fluid index metric 142A indicates a maximum detected value of 96. Although thoracic fluid index metric 142A is not contributing to risk level 144 in this example, it is provided because it is an important indicator of thoracic fluid volume and potential heart failure. Atrial fibrillation duration 142B indicates that patient 14 has had 28 days of atrial fibrillation or atrial tachycardia for 24 hours. Activity metric 142C indicates that patient 14 has been active for less than 1 hour per day for the last 4 weeks. In addition, ventricular pacing metric 142D (e.g., a cardiac resynchronization therapy percentage) indicates that IMD 16 has been pacing heart 12 less than 90 percent of the time. As patient metrics 142 indicate, information may be given that is more specific than just a threshold has been exceeded. The actual observed patient metric data, or summary of the data, may be presented in trend summary 138.

Risk level 144 is highlighted by a double-lined rectangle for easy location by the user. In other examples, risk level 144 may stand out from the rest of screen 130 in different manners. For example, risk level 144 may be of a different color, font size, or be presented with animation (e.g., flashing or scrolling). Alternatively, risk level 144 may be located at the top of screen 130 or other easily identifiable location. Although risk level 144 is generally presented as a word category, risk level 144 may be presented with a fraction, percentage, weighted average, or other numerical score that indicates that the severity of the risk level.

Although screen 130 may be a passively presented informational screen, screen 130 may be interactive. The user may select areas of screen 130 to view more details about any of patient metrics 142, e.g., the user may request diagnostic information from IMD 16. Screen 130, in other examples, may provide scroll bars, menus, and navigation buttons to allow the user to view additional information, adjust therapy, adjust metric parameters, or perform other operations related to the treatment of patient 14 with the patient metrics and risk level.

Figure 7:
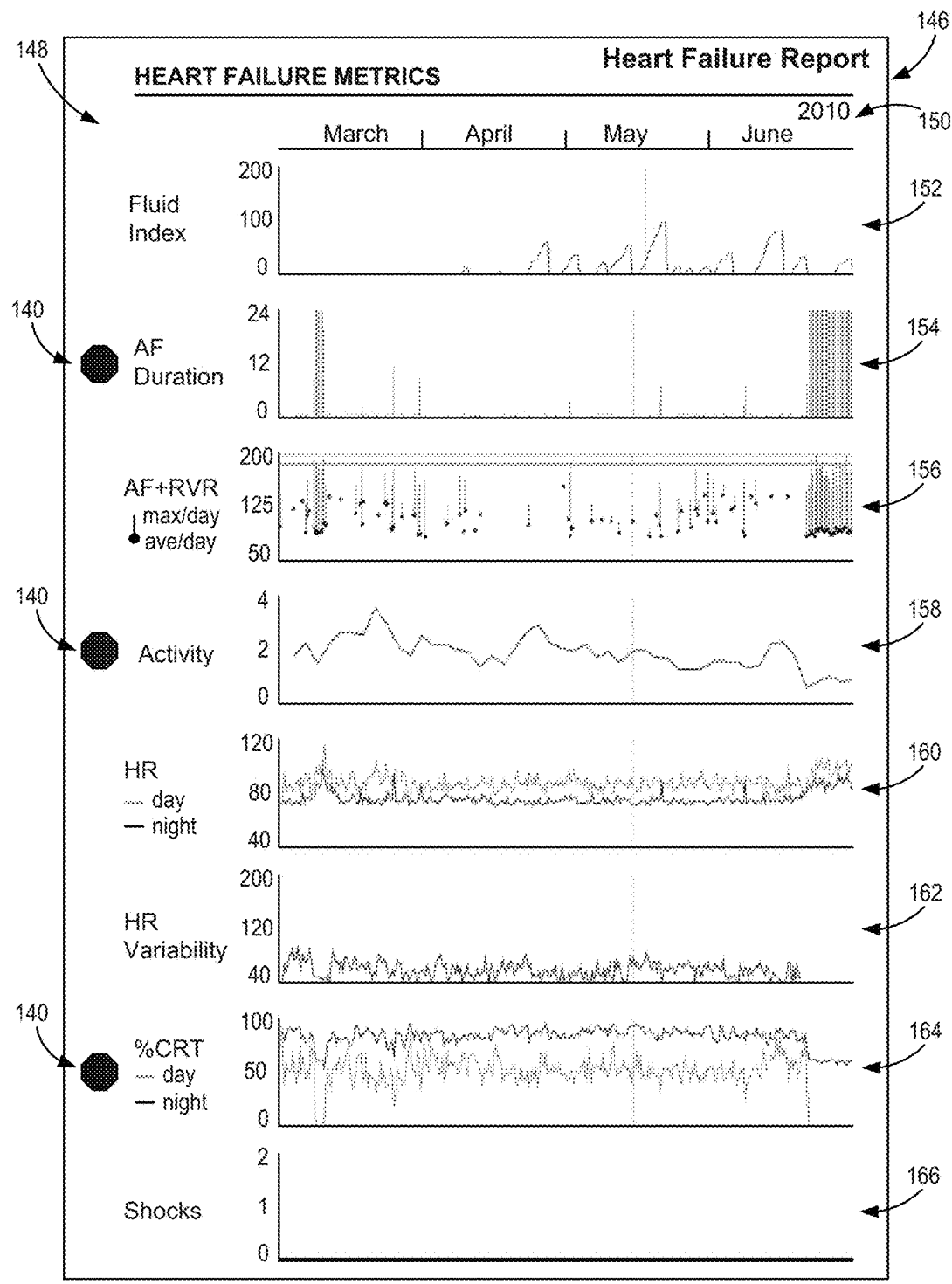
FIG. 7 illustrates an example user interface that includes exemplary heart failure data that may be used in determining heart failure hospitalization for a patient.

FIG. 7 illustrates an example screen 146 of another user interface 104 with diagnostic data. Screen 146 may include data (e.g., raw or calibrated data) from all of the patient metrics used to generate the heart failure risk level for patient 14. Although screen 146 is described as being presented on user interface 104 of programmer 24, screen 130 may be presented on any user interface of any device used by a healthcare professional. As shown in FIG. 7, screen 146 provides another heart failure report, similar to screen 130 of FIG. 6. Included are the metric data for a variety of patient metrics 152, 154, 156, 158, 160, 162, 164, and 166. Timeline 150 indicates for which months the data is representative in all the metric graphs. Although this four month period may be the evaluation window, timeline 150 may cover many evaluation windows. For example, the evaluation window may be equal to one week or one month, such that the risk level is reviewed after the evaluation window expires. In addition, the user may move through time with an interactive timeline 150 in other examples. Although not presented in screen 146, the heart failure risk level may also be presented. In some examples, the user may select any point within the graphs for the patient metrics to retrieve specific values of the patient metric at that point in time.

Thoracic fluid index metric 152 is labeled as "Fluid index." Thoracic fluid index metric 152 illustrates that the thoracic fluid index has been periodically raising and lowering over the months of May and June. In one example, the thoracic fluid index threshold may be approximately 60. However, the thoracic fluid index threshold may be generally between approximately 40 and 200.

Atrial fibrillation duration metric 154 is labeled "AF Duration" and indicates how many hours each day that the patient endured atrial fibrillation. As shown, atrial fibrillation duration metric 154 includes critical indicator 140 because of the days of atrial fibrillation shown at the end of June. An example atrial fibrillation duration threshold may be approximately 6 hours. However, the atrial fibrillation duration threshold may be set generally between approximately 1 hour and 24 hours. Ventricular contraction metric 156 is labeled "AF+RVR" and indicates the ventricular contraction rate during atrial fibrillation. The graph of ventricular contraction metric 156 provides the average ventricular contraction rate for each day and also the maximum ventricular contraction rate observed during each day. Generally, the ventricular contraction rate during atrial fibrillation threshold may be set between approximately 70 beats per minute and 120 beats per minute for 24 hours. In one example, the ventricular contraction rate threshold may be approximately equal to 90 beats per minute for 24 hours. In other examples, the duration of 24 hours may be shorter or longer.

Activity metric 158 also is highlighted with critical indicator 140. Activity metric 158 is labeled "Activity" and indicates for how many hours the patient is active each day. A patient may be considered active when, for example, the output of an accelerometer exceeds a threshold. Lower activity levels may be a risk factor for heart failure, and the graph of activity metric 158 indicates that patient 14 has been less active at the end of June. In this manner, the patient metric of activity may be a metric where exceeding the metric-specific threshold includes dropping below the threshold. In one example, the patient activity threshold may be approximately equal to 1 hour per day for seven consecutive days. In other examples, the threshold may be set to more or less time over a different duration. Instead of hours per day, other examples of activity metric 158 may provide durations of certain postures, e.g., lying down, sitting up, or standing. In general, activity metric 158 may include measurements of the rigor of patient activity and/or the amount of time patient 14 is active.

Screen 148 also provides for heart rate metrics. Heart rate metric 160 is labeled "HR" and indicates separate graphs for each of the nighttime heart rate and daytime heart rate. In some examples, the nighttime heart rate may be more indicative of heart failure risk. Generally, the nighttime heart rate threshold may be set to between approximately 70 beats per minute and 120 beats per minute for a certain period of time. In one example, the nighttime heart rate threshold may be approximately 85 beats per minute for seven consecutive days. Heart rate variability metric 162 is labeled "HR Variability" and indicates the degree of change in heart rate throughout the day. Since lower heart rate variability may indicate an increased sympathetic tone detrimental to blood flow through the vasculature, heart rate variability may also be a patient metric where exceeding the metric-specific threshold includes dropping below the threshold. In one example, the heart rate variability threshold may be set to approximately 40 milliseconds for seven consecutive days, but other variability thresholds may also be used. In other examples, screen 148 may also provide comparisons between two or more patient metrics, e.g., the difference between day heart rate and nighttime heart rate.

In addition, screen 148 may also provide a few patient metrics derived from therapy delivered to patient 14. Therapy percentage metric 164 is labeled "% CRT" and indicates the percentage of time each day and night that IMD 16 is delivering a cardiac resynchronization therapy, e.g., pacing therapy. Lower percentages of therapy may indicate diminished blood flow through the vasculature. Generally, the cardiac resynchronization therapy percentage threshold may be set to a value between 70 percent and 100 percent for a given period of time. In one example, the cardiac resynchronization therapy percentage threshold may be set to approximately 90 percent for five of seven consecutive days. Since the nighttime therapy percentage is less than 90 percent, critical indicator 140 is used to highlight therapy percentage metric 164.

In other examples, a ventricular pacing percentage may be monitored for patients receiving pacing therapy with dual or single chamber pacing devices. Increased ventricular pacing from single chamber cardiac resynchronization therapy devices may increase the risk of heart failure in some patients due to desynchronization of ventricular contractions in the heart. Conversely, lower ventricular pacing in dual chamber devices may increase the risk of heart failure in some patients.

Further, shock metric 166 is labeled "Shocks" and indicates the number of electrical shock events, e.g., cardioversion or defibrillation, endured by patient 14. As shown in FIG. 7, patient 14 has not been subjected to any shock therapy. Although the threshold may be set to a different value, the electrical shock threshold may generally be set to approximately 1 electrical shock.

Since each of patient metrics 154, 158, and 164 have exceeded their respective metric-specific threshold, critical indicator 140 is provided for each metric. In addition to, or in place of, critical indicators 140, patient metrics may be highlighted with a different text color, circles or boxes surround each metric, or some other indication of the critical level of each metric. In other examples, other patient metrics may be presented in heart failure metrics 148, e.g., blood pressure, blood glucose, lung volume, lung density, or respiration rate, weight, sleep apnea burden derived from respiration, temperature, ischemia burden, sensed cardiac event intervals, and troponin and/or brain natriuretic peptide (BNP) levels.

Although screen 148 may be a passively presented informational screen with diagnostic information, screen 148 may be interactive. The user may select areas of screen 148 to view more details about any of the presented patient metrics, for example. The user may also move to different time periods with timeline 150. Screen 130, in other examples, may provide scroll bars, menus, and navigation buttons to allow the user to view additional information, adjust therapy, adjust metric parameters, or perform other operations related to the treatment of patient 14 with the patient metrics and risk level. Further, the user may interact with the graph of each patient metric to expand the graph and view more details of the graph, perhaps even individual values.

In other examples, diagnostic information may be presented one patient metric at a time or even raw data that IMD 16 uses to generate the patient metric. For example, during a hospitalization period for patient 14, IMD 16 may transmit the detected thoracic impedances to a remote computing device of a clinician treating patient 14. IMD 16 may transmit detected thoracic impedances at a predetermined interval or in response to an interrogation request from the clinician. The predetermined interval may be generally between approximately one minute and four hours, but other predetermined intervals may be used. The clinician may use some or all of the diagnostic information to determine when patient 14 has improved enough to be discharged from a hospital setting, or whether patient 14 should be admitted to the hospital due to heart failure.

Once the risk level is generated, processor 80 generates an alert of the risk level and transmits the alert to the user via telemetry module 88 (244). As described herein, the alert may be transmitted on a schedule or as soon as communication is possible to another device or access point. In some examples, the heart failure risk level may only be transmitted when requested by a user. In some examples the alert may also include more detailed information regarding the patient metrics included in the risk level.

FIGS. 8-15 are directed to techniques that are able to more realistically predict a patient's prospective risk of HFH. By determining a patient's prospective HFH risk, medical personnel may intervene with the heart failure patient's care to avoid or reduce the chances of a patient experiencing HFH. In order to predict a patient's prospective risk of HFH, a heart failure patients' database is created and stored into memory. The heart failure patients' database is typically based on real-time data stored in each patient's IMD 16, which is then transmitted and stored into an external device's 114 memory 119. Data (e.g. a HFH that occurs during an evaluation period) is also acquired and stored into memory 119 when a patient communicates with medical personnel and/or the information accessed from the IMD 16. Based upon the real-time data obtained from each heart failure patient's IMD 16 and whether or not the patient experienced a HFH, a lookup table is formed and stored into the database.

Figure 8:
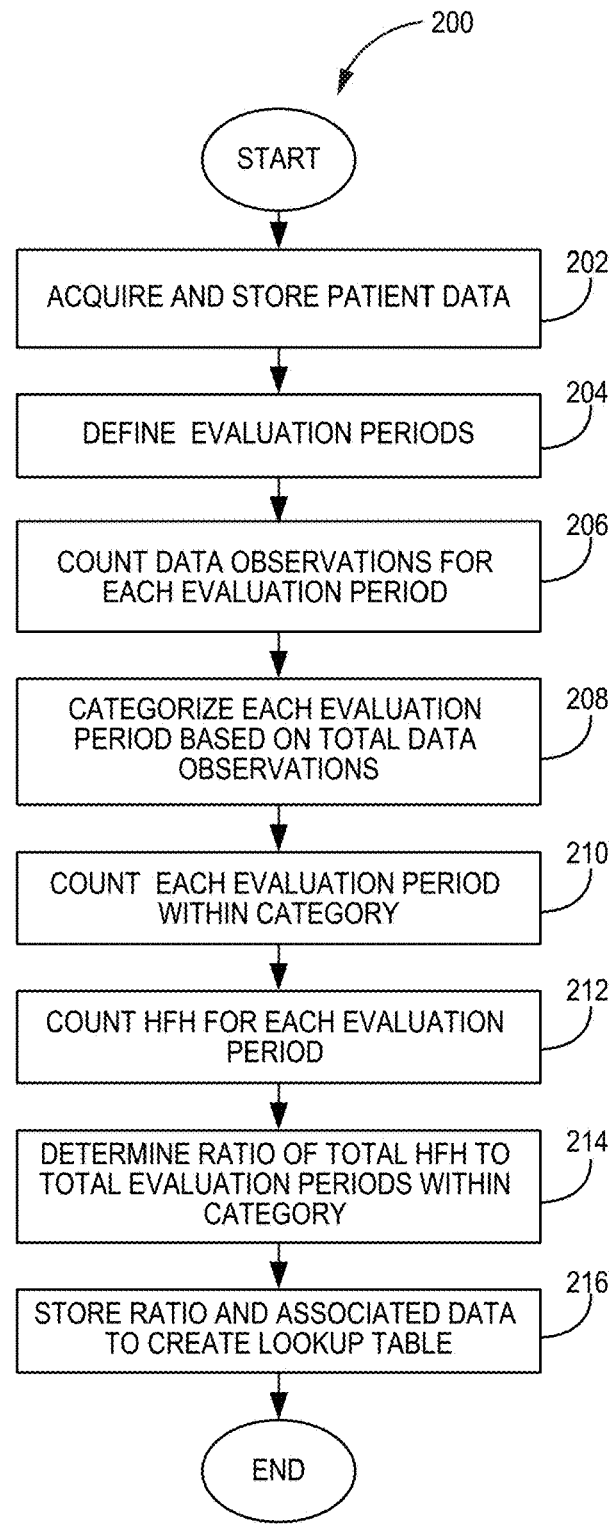
FIG. 8 is a flow diagram of an exemplary technique heart failure patient-related data organized and stored in memory that is subsequently used to predict prospective risk of heart failure hospitalization for a patient.

The flow diagram in FIG. 8 depicts an exemplary method 200 for creating a database in which data, acquired from numerous heart failure patients, is stored into memory. To better understand the manner in which the database is created, a process description is presented in which data is obtained from a single heart failure patient. The process in FIG. 8 is repeatedly performed for each patient of the total amount of patients for the database. Data is typically acquired from the implantable medical device and/or through communication between the patient and medical personnel, all of which is transmitted and stored into the database. For example, whether or not a patient experienced HFH during an evaluation period is typically known since the patient's data records were stored into memory during the hospitalization. Whether the HFH occurred at the beginning or the end of the evaluation period is irrelevant to predicting the prospective risk of HFH. The technique described herein merely determines that a HFH occurred sometime during the evaluation period.

Additionally, data, referred to as data observations, are associated with diagnostic parameters that are measured via one or more IMD 16 sensors (e.g. electrodes, chemical sensors, etc.) disposed in a patient's body at block 202. A sensor acquires data that is compared to a threshold by a processor to determine whether a metric has been detected. The detected data observation(s) are associated with a single metric or multiple metrics. Detected data is automatically stored into the memory of IMD 16. Referring to FIG. 9, Table 1 presents exemplary diagnostic parameter data and associated thresholds that may be used. Skilled artisans appreciate that the thresholds in Table 1 are examples and may be established for a group of heart failure patients or can be customized for each patient by a user of method 200.

The left column of Table 1 provides IMD parameters and associated representative trend while the right column presents an exemplary default threshold values that correspond to each diagnostic metric. Each time a threshold for a diagnostic threshold is crossed, data is automatically stored into memory, which can be accessed by the processor to generate IMD reports to be viewed by a physician via a GUI or a printed IMD report.

Diagnostic metrics, typically indicative of worsening heart failure, mortality risk and/or hospitalization risk, include an (1) impedance trend index (also referred to as OPTIVOL® commercially available in IMDs from Medtronic Inc., located in MN), (2) intrathoracic impedance, (3) atrial tachycardia/atrial fibrillation (AT/AF) burden, (4) mean ventricular rate during AT/AF, (5) patient activity, (6) Ventricular (V) rate, (7) day and night heart rate, (8) percent CRT pacing, and/or (9) number of shocks. The OPTIVOL® index is an indicator of the amount of fluid congestion experienced by the patient. The OPTIVOL® index is the difference between an impedance measured during real time using IMD 16 and a reference impedance, that can be continuously updated, established by the IMD 16 or during another visit to the physician. OPTIVOL® is described in greater detail with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein.

Table 1 further depicts an exemplary impedance signal 300 compared to a threshold 306 over a several month time period (i.e. X-axis) with a Y-axis extending from 0 to 160 ohms-days. Impedance was measured intrathoracically across the right ventricular (RV) coil and the IMD housing or can. The OPTIVOL® threshold 302 can be set at 60 ohms-days; however, the threshold can be set at another suitable value by the user. When the OPTIVOL® threshold crosses the threshold value, it signals that the patients may be at risk of congestion. The OPTIVOL® signal from the patient appears to reach 160 ohms-days sometime in January 2009 as the reference impedance stays above the raw impedance, and then drops below the threshold thereafter as raw impedance goes higher than the reference impedance.

Impedance is yet another diagnostic parameter used to predict HFH. Impedance, as a diagnostic parameter, is measured against a baseline signal 306 as a threshold level. Relative to the value of the baseline signal 306, an increase in fluid volume and associated increase in wedge-pressure correlates with a reduction in intrathoracic impedance. In contrast, a decrease in fluid volume and associated decrease in wedge-pressure correlates with an increase in intrathoracic impedance relative to the baseline value.

Another exemplary diagnostic parameter relates to AT/AF. Atrial fibrillation (AF) burden is measured as total duration of fast atrial rate during a 24-hour period associated with atrio-ventricular conduction ratio≥2:1. Fast atrial rate is typically associated with rates 150 bpm or faster. About 60 bpm is normal for day-time and 40-50 for night-time while 70 bpm is typically associated only with children. Likewise, if the patient has heart block then the atrial rate could beat at, for example, 90 bpm while the RV and LV maintain a normal rhythm at 60 bpm. Fast atrial rate can also be defined as faster than the RV rate.

The AT/AF threshold indicates that a patient has AT/AF for a continuous minimum amount of time. For example, the AT/AF threshold is exceeded when a patient experiences AT/AF for greater than 6 hours during a day.

Average ventricular rate during AT/AF (VRAF) threshold is yet another diagnostic parameter that can be used to predict whether a patient is experiencing worsening HF such that the patient is subject to increased risk of HFH. VRAF is typically measured during AF over a 24-hour time period. The V rate can be defined as beats per minute (bpm) which is the time from R-wave to R-wave. The V rate during AT/AF threshold is designated as a time period in AT/AF is greater than or equal to 6 hours and a mean V-rate greater than 100 bpm.

Patient average activity is yet another useful diagnostic parameter for predicting risk of HFH. Activity, a surrogate of functional capacity, is a quantitative measure of active duration during a pre-specified time period. Lower activity (e.g. average activity for at least 1 week is less than 1 hour per day) can signal compromised functional capacity. If the patient average activity is less than one hour per day over a week's period, the patient is at increased risk of worsening HF.

Yet another useful diagnostic parameter is V rate measured in beats per minute (bpm). V rate uses a threshold that relies on night heart rate (NHR). NHR, a marker of autonomic tone, can be associated with increased risk of HFH if the NHR is elevated. NHR measures the average resting heart rate between midnight and 4 AM. The threshold for NHR is greater than 85 bpm for the most recent seven days of data collection.

Heart rate variability (HRV), measured in milliseconds, and elevated NHR can be used as markers of imbalance in autonomic tone. HRV less than 50-60 ms is potentially a marker of elevated sympathetic tone and/or imbalance in sympathetic and parasympathetic tones. Still yet another exemplary parameter threshold is the percent pacing in which V pacing less than 90% since the last or previous session which is only applicable to CRT pacing devices. V pacing is the amount of ventricular pacing delivered. The IMD also records other data such as percent CRT pacing delivered during a day, number of VT episodes, and whether the patient received a defibrillation shock.

At block 202, patient data is acquired and stored into memory. For example, patient data can be transmitted and stored into memory 119 of external device 114 via telemetry from an IMD 16. The patient data, obtained from clinical trials referred to as FAST and PARTNERS-HF, associates data observations with any HFHs (i.e. 220 HFHs) that may have occurred in a patient. FAST was a prospective double-blinded observational study in patients (n=109) using Medtronic CRT-D or ICD devices with EF≤35% and NYHA class III or IV. PARTNERS-HF was a prospective observational study enrolling patients (n=1024) with CRT-D devices with EF≤35%, NYHA class III or IV, and QRS duration≥130 ms.

Exemplary patient data used to create the database can be shown by the set of timeline data obtained from patients 1, 2, and 3, depicted in FIG. 13A. Each patient timeline shows data observations that occurred during first and second time periods (i.e. $FU_X$, $FU_{X+1}$) within a look back period. Patient 1 triggered data observations related to an activity threshold (e.g. average activity for at least 1 week is less than 1 hour per day) during $FU_X$. A defibrillation shock was delivered to the patient during $FU_{X+1}$. Accordingly, both $FU_X$, $FU_{X+1}$ for patient 1 would be classified as evaluation periods that should be placed in the 1 data observation category. Patient 2 triggered data observations related to OPTIVOL® during the first time period (i.e. $FU_X$) while CRT, and NHR, were triggered in the next or second time period (i.e. FUx+1). Patient 3 triggered data observations related to CRT during the first evaluation period, while OPTIVOL®, and activity were triggered during the second evaluation period. Differentiation is not made between type of data observation (e.g. activity, NHR, shock, OPTIVOL®, CRT etc.); therefore, any type of data observations triggered during an evaluation window is counted at 206.

Patient data, shown in the timelines of FIG. 13A, is summarized in the columns (depicted in FIG. 13B) that represent 0, 1, 2, and more than 2 data observations. For example, column 1 represents the zero data observations category from all patients. Each horizontal line in column 1 indicates the duration for which 0 observations occurred for each evaluation period. An evaluation period or window is placed or slotted into column 1 if a determination is made that an evaluation window had zero data observations. Column 1 also indicates that two of the ten evaluation periods included a HFH. Accordingly, the HFH risk for the zero observation category is 2/10 or 0.2, which is a 20% risk of HFH.

Column 2 is associated with FUs in which one (1) data observation has been triggered, column 3 is associated with FUs in which two (2) data observations have been triggered, and column 3 is associated with FUs in which three (3) data observations have been triggered. HFH risk for each of the observation categories can be computed by noting the proportion of all evaluation windows that has an HFH.

After data is stored in the database, the computer system defines a look back period as a set of evaluation time periods at block 204 in FIG. 8. For example, the look back period for a patient includes two consecutive evaluation periods—a preceding evaluation period and a current evaluation period. In one or more embodiments, each evaluation period extends the same amount of time (e.g., 30 days, 45 days, 60 days, 75 days, 90 days etc.). In one or more other embodiments, evaluation periods may extend a different amount of time, which provides a variable look back period. For example, one evaluation period can be 30 days while another evaluation time period may be 35 days. The user of method 200 determines whether a variable or invariable evaluation period is used during the look back period.

Each evaluation period is categorized by total amount of data observations experienced by that patient during that evaluation period at block 208. To categorize or classify the evaluation period, data observations (e.g. 0, 1, 2, 3, etc.) are counted at block 206. For example, if 0 data observations exist during the evaluation period, the evaluation period is designated as 0 data observations. A counter, associated with the zero data observations category, is then incremented by "1" to indicate that the evaluation period has been determined to have zero data observations. The zero data observations category counter continues to be incremented when other evaluation periods have zero data observations.

During or after categorizing all of the evaluation periods, each evaluation period, within a particular data observations category, is then counted at block 210. After totaling evaluation periods that are within a data observations category (e.g. 0 data observations category, 1 data observations category, 2 data observations category, 3 data observations category etc.), the total amount is stored into the database. Once all of the evaluations periods have been processed, the counting process is then terminated.

At the same time or about the same time, a determination is made as to whether a HFH had occurred for each evaluation period experienced by a patient at block 212. If a HFH was experienced by a patient during the current evaluation period for a patient, a HFH counter for that particular data observations category is incremented by "1." Additionally, the processor tracks the data observations category for which the HFH and the time period in which the HFH occurred.

The prospective risk of HFH is then estimated at 214 for each data observation category. For example, the equation for estimating HFH risk for each evaluation period, designated with 0, 1, 2, 3, or more data observations, is as follows:

$$\frac{\text{Number of Risk Prediction windows with} \geq 1\ HFH}{\text{Total number of Risk Assessment windows}}$$

or, stated in another way, as follows:

HFH risk=(HFHnext)/Nnext where HFHnext is the total amount of HFH that occurred during the current prediction period (shown as "HFH" in FIG. 13B) for that particular data observations category while Nnext represents the total number of evaluation windows (also referred to as "risk assessment windows" or "risk prediction windows") that is associated with that particular data observations category.

Thereafter at 216, a lookup table (FIG. 13C) is created that associates total data observations during an evaluation period with prospective risk of heart failure hospitalization shown as a decimal or a percentage. After patient data from all of the heart failure patients have been processed, the database is deemed complete. Skilled artisans appreciate that while the database may be considered complete, the database can be configured to be updated to include additional patient data or diagnostic data from the device.

Figure 14:
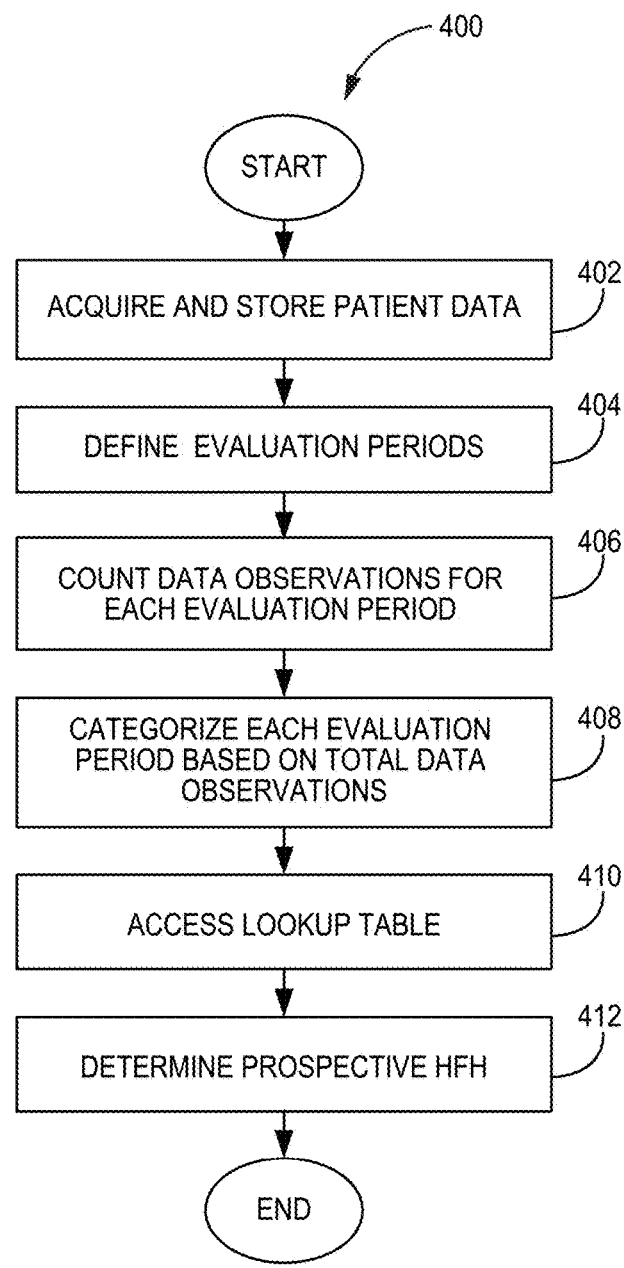
FIG. 14 depicts a flow diagram that predicts prospective risk of heart failure hospitalization for a patient.

After the database has been completed, a patient's prospective risk of heart failure hospitalization can be estimated using the lookup table stored into memory. For example, method 400 shown in FIG. 14, shows prospective HFH risk estimated for a patient. Patient data can be acquired through an IMD 16 or other suitable means at block 402. At block 404, a look back period is established. A look back period is comprised of a set of consecutive evaluation periods. The set of evaluation periods includes a first evaluation period (also known as a preceding evaluation period) and a second evaluation period (also known as a current evaluation period) etc.).

Data observations that occurred during the preceding evaluation period are counted at 406 to determine a total amount of data observations. Additionally, data observations are counted for the current evaluation period to determine a total amount of data observations. At block 408, each evaluation period is categorized based upon the total data observations. Using the total data observation category, the lookup table is accessed by the processor. The processor searches for the total observation category within the lookup table at 410 and then determines the heart failure hospitalization risk associated with the total observations at 412. The process of looking up each HFH risk from the look up table is repeated for each evaluation period. In one or more embodiment, the HFH risk is determined for each evaluation period by the processor search for the risk percentage shown in the lookup table in FIG. 13.

In one or more embodiments, a prospective heart failure hospitalization risk is determined by using weighting factors. For example, weighting factors can be used in which the latter evaluation time period is weighted more heavily than an earlier evaluation time period. For example, the weighting factor for a latest occurring evaluation time period (i.e. current evaluation period) ranges from 0 up to 0.9. A weighting factor for an evaluation time period (i.e. preceding evaluation period) ranges from 0 up to 0.5 compared to the latter evaluation period (i.e. current evaluation period). In one or more other embodiments, weighting factors can be used to adjust for an evaluation period that extended for a shorter period of time compared to another evaluation period which was longer. For example, a short evaluation period (e.g. extended a total of 30 days) could be multiplied by 0.50 (i.e. using a ratio equation, 30/60) of a long evaluation period of 60 days). After determining the HF risk, a graphical user interface displays the patient's prospective heart failure hospitalization risk to the user.

Based upon the predicted HFH risk, a notification can be automatically generated to the physician indicating that the patient has a substantial risk of hospitalization and needs to be evaluated. Notifying the physician to intervene can prevent or reduce HFH, which can potentially improve long-term patient outcome while reducing costs of care. Additionally or alternatively, the physician can perform additional clinical evaluation of the patient or the cardiac therapy can be wirelessly adjusted. In an alternate embodiment, the cardiac therapy is automatically adjusted based upon pre-specified criteria determined at implant or during a follow-up visit.

Figure 10:
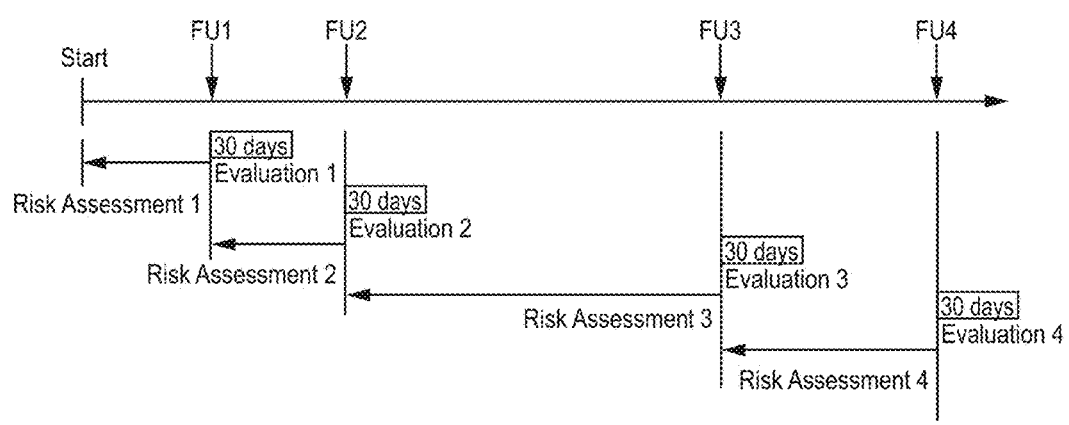
FIG. 10 depicts exemplary heart failure hospitalization risk assessments that depend upon duration and amount of data observations for heart failure patients.
Figure 12:
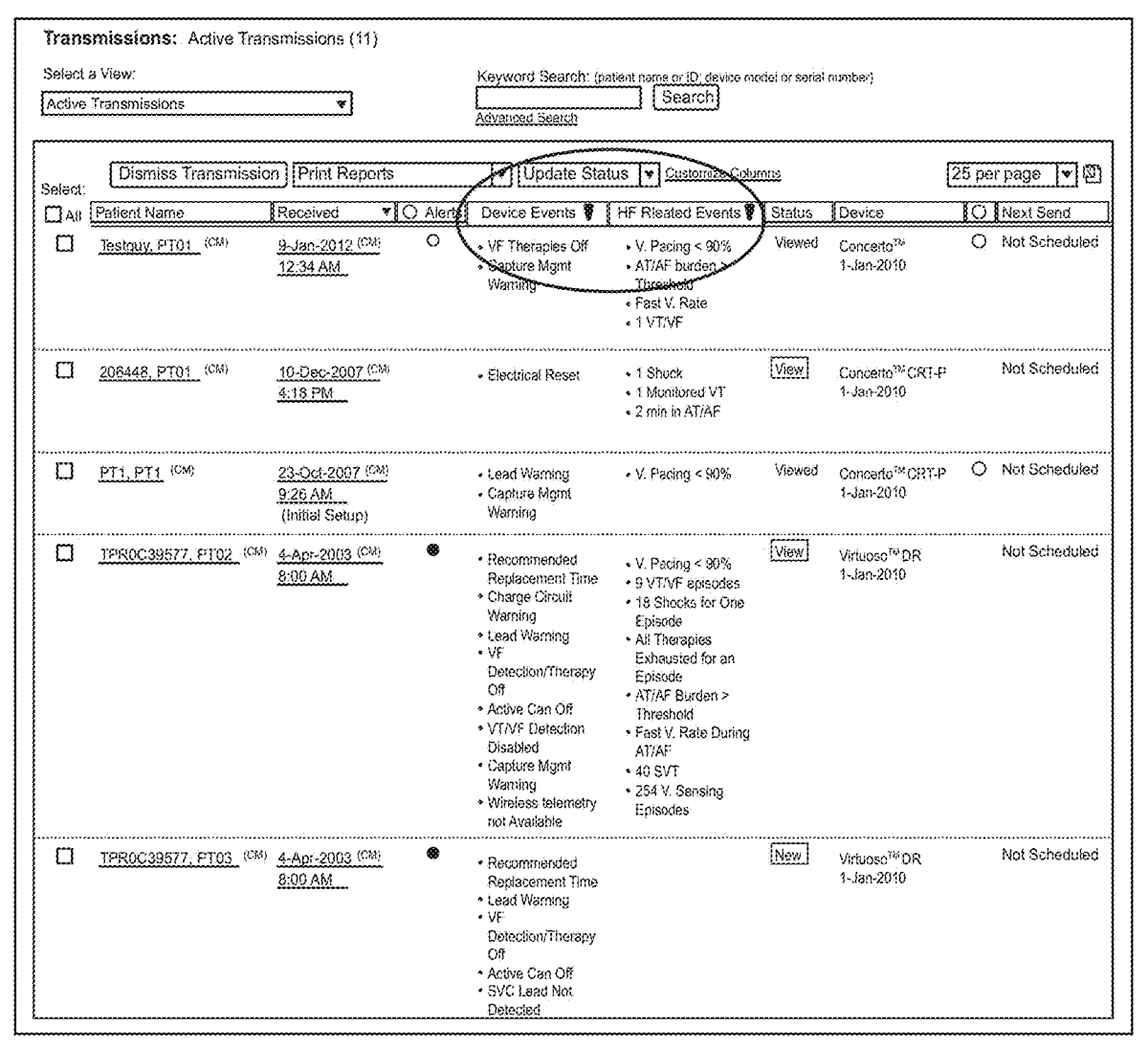

While determining the prospective HFH risk is important, the manner of conveying information as efficiently as possible may save time for the physician. FIGS. 10, 12, and 15 are exemplary graphical user interfaces that can be displayed to a user. FIG. 10 provides a graphical user interface that includes a set of exemplary HFH risk assessments for a single patient over a longer period of time. The set of exemplary risk assessments are shown for each follow-up visit (FU1-FU4) over a pre-specified time period (e.g. thirty day period). A follow-up visit occurs at a single point in time whereas a time period between two consecutive follow-up visits is referred to as a risk evaluation window or as a risk prediction window. Follow-up visit 1 (FU1) starts at time zero and ends thirty days after the start time. Follow-up visit 2 (FU2) starts at the end of FU1 and ends thirty days thereafter. Follow-up visit 3 (FU3) starts at the end of FU2 and extends thirty days after the start time of FU3. Follow-up visit 4 (FU4) starts at the end of FU3 and extends thirty days after the start time of FU4. The duration of the risk assessment windows for each follow-up session are shown by the horizontal length of each risk assessment shown in FIG. 10.

The duration of the risk assessments for FU1 and FU2 is about the same, as is depicted by horizontal lengths of each risk assessment being about the same in length. The risk assessment duration for FU4 is greater than FU1 and FU2, while the FU3 risk assessment duration is substantially greater than all risk assessments shown in FIG. 10. Prospective risk assessments for HFH are shown by arrows, pointed from the end of each FU period to their respective start time, to reflect that the risk assessment depends on retrospective data. The retrospective data is the data observations from that evaluation period. As previously stated, prospective HFH risk (i.e. the next 30 days, etc.) requires that the processor to look back to the evaluation period and determine the data observations experienced by the patient. The look up table, stored in memory 119 of external device 114, is accessed based upon the total data observations and then the prospective HFH risk is determined.

In an alternative embodiment, an evaluation is performed of all triggered diagnostic data extending from time equal zero (e.g. implant of the IMD). While all current and most recent previous follow-ups start from time equals zero, each FU time period ends at a different time. Under this scenario, the risk prediction window extends from FU1 to FU2 which is thirty days; the risk prediction window extends from FU2 to FU3 which is 60 days; the risk prediction window extends from FU3 to FU4 which is 90 days, and the risk prediction window extends from FU4 to another point in time which may be 120 days. The embodiment that includes longer time periods may provide trend data that extends for a greater time period, which some physicians may consider to be useful. In one or more embodiments, the physician can switch between graphical user interfaces showing the most recent data alone or data which provides longer trend information.

One or more embodiments of FIG. 10 can be applied such that, for example, the current evaluation period extends from a time indicated by the arrow head of FU2 to the arrow head of FU1. The preceding evaluation period extends from a time indicated by the arrow head of FU1 to the start. In this example (shown in FIG. 10 in bold and capitalized text), the current and preceding evaluation periods are used to predict the 30 day prospective risk immediately after the current evaluation period.

FIG. 12 is yet another user interface displaying data content to a user. The data content is parsed into device events and heart failure related events. One user may be more interested in device events while another user may be more interested in the heart failure related events. The device events can be accessed by clicking on the tab with term "device events" displayed thereon. The device events include, but are not limited to, VF therapies off, a capture management warning, electrical reset, a warning about a lead issue, recommended replacement time for the device, a charge circuit warning, VF detection therapy off, active can (or housing) off, VT/VF detection disabled, wireless telemetry not available, SVC lead not detected.

FIG. 15 is yet another user interface that provides alerts when certain prescribed events occur relative to a patient. User interface tabs are provided to allow the user to quickly access the data of most concern to that user. The user interface displays tabs relate to overview data, alert groups, clinic management alerts (e.g. red, yellow and web-site only alerts), and notification hours. Red alert means a very important threshold has been crossed whereas a yellow alert means the item is of concern.

On the left hand side of the user interface is a list of items related to clinic management alerts. The list is parsed into data observations and device items. The list of data observations includes AT/AF daily burden greater than threshold, average ventricular rate during AT/AF, number of shocks delivered in an episode, and all therapies in the zone exhausted. Multiple clinical events include time in AT/AF greater than or equal to a predetermined number of hours per day, time in AT/AF greater than or equal to a predetermined number of hours and mean V-rate greater than a prespecified level for a least one day, NHR greater than 85 bpm for all or most of 7 days, average activity for at least one week is less than 1 hour per day, at least 1 VT/VF shock, ventricular pacing (VP) less than 90% since the last transmission (only visible for CRT devices), a prespecified number of events occurred from the list, and user selected number (1-6 items) of events occurred. The user could enter a number (e.g. 1-6 items), as shown, or a drop down menu can be used to have the user select a number of items. The range of numbers provided reflects how many events in the list have been checked by the user.

Skilled artisans would appreciate that any number of boxes in FIG. 15 can be checked or unchecked to indicate an event or alert has occurred. FIG. 15 illustrates only one possible scenario. For example, unchecked events include time in AT/AF≥[x] hours for at least 1 day, and NHR>85 bpm for all of the most recent 7 days. Checked events include time in AT/AF≥X amount of pre-specified number of hours] hours and Mean V-Rate>y amount of pre-specified number of hours] for at least one day, average activity for at least 1 week is <1 hour/day, at least one VT/VF shock, and VP<90% since last transmission.

The device list includes lead/device integrity issues, VF detection therapy off, low battery voltage warning indicating a recommended replacement time for the device, excessive charge time for end of service, right ventricular lead integrity, right ventricular noise, atrial pacing impedance out of range, and right ventricular pacing impedance out of range.

In order to avoid obscuring techniques of the invention, details as to the database stored in memory 119 of external device 114 is presented below. The HFH risk assessment effectiveness data was established through the use of two combined so clinical studies referred to as FAST and PARTNERS. Table 2, presented below, summarizes the patient demographics for the 775 patients in FAST and PARTNERS trials that were used for the present analysis. All patients had CRT-D IMDs and the majority (87%) of the patients exhibited heart failure status of NYHA III. Additionally, the patients had similar characteristics of a patient population receiving cardiac resynchronization therapy.

Table 2 summarizes patient demographics in which FAST and PARTNERS-HF trials were combined for the present analysis. The majority of patients were classified as NYHA III with a mean age of 69. The majority of patients also experienced a variety of diseases (e.g. ischemic, coronary artery disease, hypertension, diabetes etc.) typically associated with HF patients and take a variety of medications (e.g. Angiotensin converting enzyme inhibitor/Angiotensin receptor blocker (ACE/ARB), beta-blockers, diuretics, digoxin, aldosterone etc.)

| Table 2 summarizes demographic characteristics' of patients | |
|---|---|
| Demographic characteristic | Total (n = 775) |
| Mean Age (SD) | 69 (11) |
| Mate Gender | 524 (68%) |
| NYHA | |
| I | 9 (1%) |
| II | 59 (8%) |
| III | 674 (87%) |
| IV | 33 (4%) |
| Ischemic | 485 (63%) |
| Coronary Artery Disease | 524 (68%) |
| Myocardial Infarction | 360 (46%) |
| Hypertension | 552 (71%) |
| Diabetes | 324 (42%) |
| History of AF | 219 (28%) |
| LVEF ≤35% | 676 (99%) |
| Baseline Medications | |
| ACE/ARB | 641 (83%) |
| Beta-Blockers | 696 (90%) |
| Diuretics | 642 (83%) |
| Digoxin | 279 (36%) |
| Aldosterone | 257 (33%) |
| AAD | 138 (18%) |
| Warfarin | 183 (24%) |

Tables 3-7 summarize some of the data from the clinical trials. Risk stratification is shown for 775 patients and 2276 follow-up sessions for numerous IMD parameters, excluding impedance (Table 3) as compared to data that includes impedance (Table 4). Table 3 includes a number of data observations (i.e. IMD observations), a number of patients who attend follow-up visits to be evaluated by a physician, a number of HFHs experienced, percentage of HFHs, GEE adjusted HFHs (95% confidence level (CI)) and odds ratio versus 0 observation (95% CI).

As is evident from Table 3, the rate of HFH increased with increasing number of data observations. For example, when no IMD observations were triggered, the 30-day event rate was 0.9% and increased to 13.6% for three or more IMD observations triggered. A vast majority (~71%) of the total follow-up sessions had no IMD observation. Additionally, the proportion of follow-up sessions with increasing observations monotonically decreased (23.5%, 4.3% and 1.3% for 1, 2 and ≥3 observations, respectively).

| Table 3 is performance of data observations excluding OPTIVOL ® in stratifying patients at the risk of heart failure hospitalization (HFH). | | | | |
|---|---|---|---|---|
| Number of Device Observation(s) | Number of follow-ups (Number of patients) | Number of HFHs (%) | GEE adjusted HFHs (95% CI) | Odds Ratio versus 0 observation (95% CI) |
| 0 | 1614 (631) | 14 (0.8%) | 0.9% (0.5-1.6) | Reference group |
| 1 | 535 (284) | 17 (3.2%) | 3.0% (1.8-5.0) | 3.6 (1.6-7.8) |

Table 3 is performance of data observations excluding OPTIVOL ® in stratifying patients at the risk of heart failure hospitalization (HFH).

| Number of Device Observation(s) | Number of follow-ups (Number of patients) | Number of HFHs (%) | GEE adjusted HFHs (95% CI) | Odds Ratio versus 0 observation (95% CI) |
|---|---|---|---|---|
| 2 | 98 (71) | 7 (7.1%) | 7.0% (3.4-13.8) | 8.5 (3.3-22.3) |
| ≥3 | 29 (24) | 4 (13.8%) | 13.6% (5.5-30.0) | 17.9 (5.6-57.2) |

Univariate analysis for various parameters as a predictor of HFH is shown in Table 4. Diagnostic parameter data that was evaluated included activity, NHR, AF burden, VRAF, decrease in CRT pacing, shock, and OPTIVOL®. Data observations for each parameter are indicated to have occurred with a "yes" denoted in a particular row, while a lack of data observations are indicated by "no." The number of FUs, and HFHs that are associated with the data observations for a particular parameter is also provided. From the tabulated data, data observations pose an increased risk of HFH as opposed to lack of data observations. Additionally, the tabulated data shows that HFH rate varies from 4.6% (for decrease in CRT pacing) to 11.2% (for VRAF) for various parameters. For activity, AF burden, and V-pacing that triggered during a large proportion of follow-up sessions (~10% or more) the event rate was 5.1%, 4.7% and 4.6%, respectively.

Table 4 univariate analysis and risk of various device parameters for HFH

| Device Observation | Number of Follow-ups | Number of HFHs (%) | GEE (95% CI) |
|---|---|---|---|
| Activity | | | |
| Yes | 277 | 14 (5.1%) | 5.1% (3.0-8.4) |
| No | 1999 | 28 (1.4%) | 1.4% (0.9-2.1) |
| NHR | | | |
| Yes | 28 | 2 (7.1%) | 7.2% (2.2-21.7) |
| No | 2248 | 40 (1.8%) | 1.8% (1.3-2.5) |
| AF Burden | | | |
| Yes | 235 | 11 (4.7%) | 4.7% (2.5-8.5) |
| No | 2041 | 31 (1.5%) | 1.5% (1.0-2.2) |
| VRAF | | | |
| Yes | 26 | 3 (11.5%) | 11.2% (3.8-28.5) |
| No | 2250 | 39 (1.7%) | 1.7% (1.2-2.4) |
| Decrease in CRT Pacing | | | |
| Yes | 228 | 11 (4.8%) | 4.6% (2.4-8.4) |
| No | 2048 | 31 (1.5%) | 1.5% (1.0-2.2) |
| Shock | | | |
| Yes | 26 | 2 (7.7%) | 7.1% (1.5-27.3) |
| No | 2250 | 40 (1.8%) | 1.8% (1.3-2.5) |
| OPTIVOL ® | | | |
| Yes | 783 | 28 (3.6%) | 3.5% (2.4-5.2) |
| No | 1493 | 14 (0.9%) | 0.9% (0.6-1.6) |

Risk stratification performance of various parameters including OPTIVOL® in 775 patients and 2276 follow-up sessions is shown in Table 4. Similar to the parameter set that excludes OPTIVOL®, the event rate of HFH increased with increasing number of observations. The event rate for the scenario of no IMD observation was 0.4% and increased to 13.6% for three of more observations. Follow-up sessions with zero IMD observations constituted the largest proportion (48.5%) of all follow-up sessions and the proportion declined with increasing number of IMD observations (36.4%, 12.2% and 2.9% for 1, 2 and ≥3 observations, respectively). In the univariate analysis, the OPTIVOL® index was found to have an HFH event rate of 3.5% as shown in Table 4.

Table 5 is performance of data observations including OPTIVOL ® in stratifying patients at the risk of heart failure hospitalization (HFH).

| Number of Device Observation(s) | Number of follow-ups (Number of patients) | Number of HFHs (%) | GEE adjusted HFHs (95% CI) | Relative Risk versus 0 observation |
|---|---|---|---|---|
| 0 | 1103 (554) | 4 (0.4%) | 0.4% (0.1-1.0) | Reference group |
| 1 | 828 (514) | 14 (1.7%) | 1.7% (0.9-3.0) | 4.6 (1.4-14.5) |
| 2 | 279 (190) | 15 (5.4%) | 5.3% (3.1-8.8) | 14.9 (5.2-43.1) |
| ≥3 | 66 (50) | 9 (13.6%) | 13.6% (7.2-24.3) | 42.4 (12.6-142.1) |

Figure 11A:
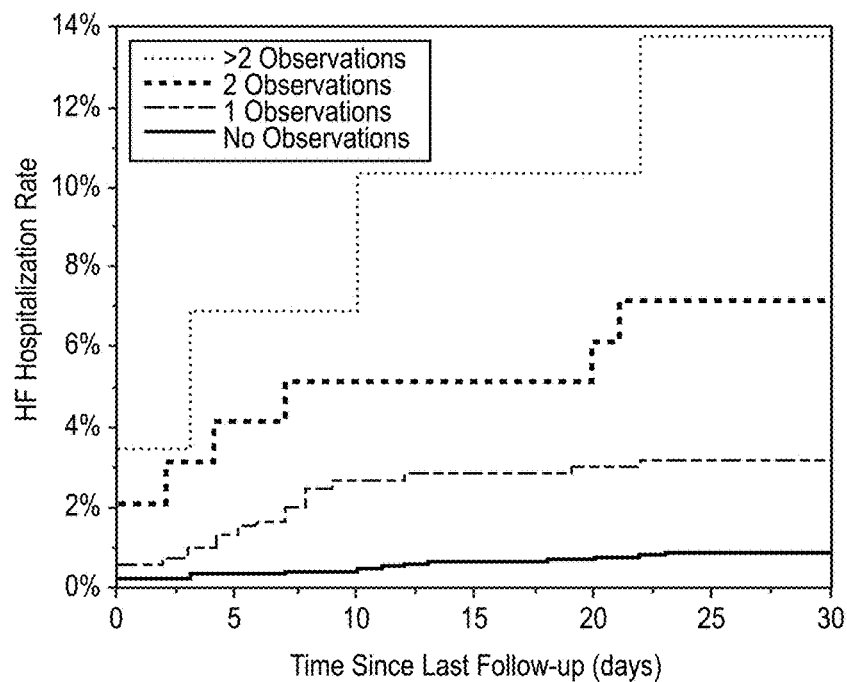
FIGS. 11A-11B graphically depict heart failure hospitalization event rates to number of diagnostic data observations in which impedance trend is excluded (FIG. 11A) and impedance trend is included (FIG. 11B).
Figure 11B:
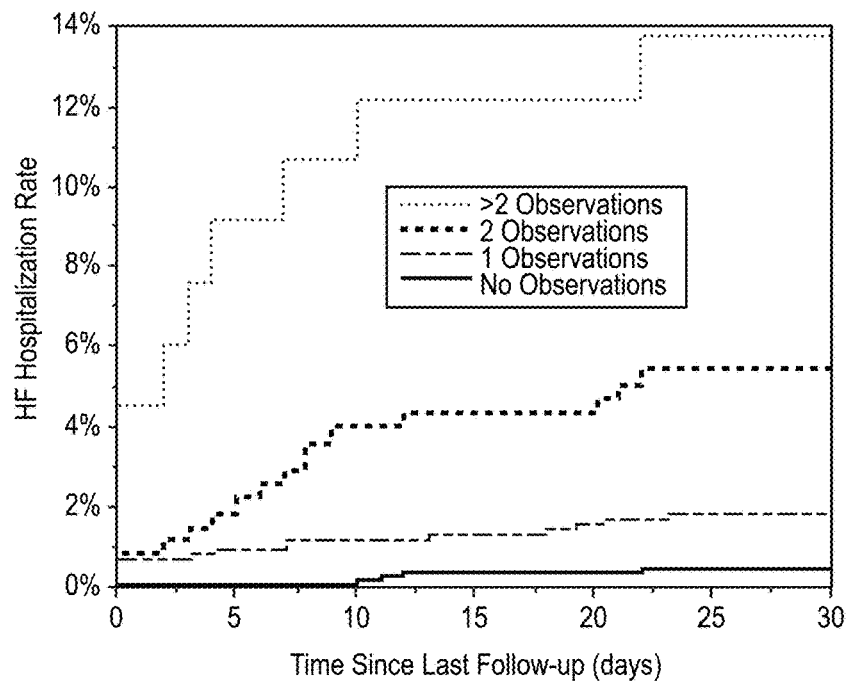

FIGS. 11A-11B shows HFH event rate in the 30-days post-evaluation for the IMD parameters excluding OPTIVOL® (FIG. 11A) and including OPTIVOL® (FIG. 11B). Kaplan Meier curves for 0, 1, 2, and 2 data observations are shown from time 0 to 30 days along the X-axis and HFH rate of hospitalizations from 0% to 13% along the Y-axis after diagnostic evaluation for various number of data observations. The increase in event rate with increasing number of observation is evident in FIGS. 11A-11B.

Tables 6 and 7 show the sensitivity and specificity of method 200 in predicting HFHs for the parameter set in which OPTIVOL® is included or excluded from the data observations ranging from 1, 2 and ≥3. For the parameter set excluding OPTIVOL®, the sensitivity for ≥1 observation was 68.9% and decreased to 9.5% for ≥3 observations. The corresponding specificity for ≥1 observation was 71.2% and increased to 98.8% for ≥3 observations. Similarly, for the scenario when OPTIVOL® was included, the sensitivity for ≥1 observations was 90.5% and decreased to 21.6% for 3 observations. The corresponding specificity increased from 49.1% (≥1 observations) to 97.4% (≥3 observations). OPTIVOL® data included the relative increase in sensitivity for ≥3 observations was significant (21.6% vs. 9.5%; see the bottom most rows in Tables 5 and 6) compared to decrease in specificity (97.4% vs. 98.8%).

with more stringent criterion of increasing numbers of observations the sensitivity worsens. For example, sensitivity with greater than or equal to three IMD observations is lower than ≥2 observations because a few hospitalizations are not captured in greater than or equal to 3 IMD observations i.e. they occur with lower number of IMD observations. Sensitivity and specificity for greater than or equal to 3 IMD observations without OPTIVOL® are 9.5% and 98.8%, respectively. For an IMD with OPTIVOL®, the corresponding sensitivity improves substantially to 21.6% while the specificity drops slightly to 97.4%.

Since IMD data is continuously or periodically collected, HFH risk can be predicted in real-time while in an ambulatory setting. For example, the patient can be assessed in an in-clinic setting. Alternatively, the IMD data can be transmitted to the clinic either automatically when a specific alert (e.g. Medtronic, Inc. CAREALERT® in CARELINK SYSTEM®) has occurred or can be transmitted by the patient on a predetermined schedule chosen by the clinician. Thus, a dynamic HF risk assessment can be made available to the clinician that can then be used along with other clinical information to manage patient's HF.

Various IMD diagnostic parameters in the IMD are a reflection of various underlying physiological processes. Deviation of a given parameter beyond a certain range may

TABLE 6

Sensitivity versus specificity in a 30-day evaluation framework for 0, 1, 2 and ≥3 observations for the parameter set excluding OPTIVOL ®.

| No. of Data observations | Sensitivity | | Specificity | |
|---|---|---|---|---|
| | Unadjusted | GEE adjusted (95% CI) | Unadjusted | GEE adjusted (95% CI) |
| ≥1 Observation(s) | 28/42 (66.7%) | 68.9% (52.8-81.5) | 1600/2234 (71.6%) | 71.2% (68.4-73.9) |
| ≥2 Observations | 11/42 (26.2%) | 27.0% (15.2-43.3) | 2118/2234 (94.8%) | 94.5% (93.1-95.7) |
| ≥3 Observations | 4/42 (9.5%) | 9.5% (3.7-22.5) | 2209/2234 (98.9%) | 98.8% (98.2-99.3) |

TABLE 7

Sensitivity versus specificity in a 30-day evaluation framework for 0, 1, 2 and ≥3 data observations for the parameter set including OPTIVOL ®.

| No. of Data observations | Sensitivity | | Specificity | |
|---|---|---|---|---|
| | Unadjusted | GEE adjusted (95% CI) | Unadjusted | GEE adjusted (95% CI) |
| ≥1 Observation(s) | 38/42 (90.5%) | 90.5% (77.5-96.3) | 1099/2234 (49.2%) | 49.1% (46.5-51.7) |
| ≥2 Observations | 24/42 (57.1%) | 58.0% (42.0-72.4) | 1913/2234 (85.6%) | 85.5% (83.5-87.4) |
| ≥3 Observations | 9/42 (21.4%) | 21.6% (11.2-37.6) | 2177/2234 (97.4%) | 97.4% (96.5-98.1) |

In addition, the look back period for assessing diagnostics was taken as the entire duration between the follow-up periods to mirror real world clinical practice. The risk of an HFH event with increasing number of IMD observations. For example, a patient has 18 times to 42 times increased HFH risk when three or more data observations have occurred during a FU time period compared to a patient with no observation depending on whether the IMD parameter set excludes or includes OPTIVOL® as indicated by Tables 2 and 4, respectively. The sensitivity and specificity for varying numbers of observations exhibits a trade-off between the two or more metrics such that as the specificity improves signal a compromise in physiological homeostasis and hence be a marker of patient risk. For example, impedance is an indicator of fluid status. A drop in impedance and accompanied rise in OPTIVOL® index is indicative of possible fluid overload, while an excessive rise in impedance and drop in OPTIVOL® index might signal dehydration. Similarly, elevated NHR and abnormal HRV are potential markers of imbalance in autonomic tone, and lower activity can signal compromised functional capacity. While each diagnostic parameter is a marker of risk, the prognostic value is improved when diagnostic parameters are combined as shown by comparing Table 3 to Tables 2 and 4.

One or more embodiments of the present disclosure employ an incremental approach to predicting prospective risk based solely on increasing number of observations such as 0, 1, 2, ≥3 data observations). Additionally, while a clinically relevant 30-day period is employed for HF risk prediction, the look back period for evaluating IMD diagnostics differs in that all data is used between the previous and current follow-up sessions for the same patient. In one or more other embodiments, the look back period for evaluating IMD diagnostic data differs in that all data is used between the previous and current follow-up sessions for similarly situated patients.

The present disclosure is advantageous to health care provider since the present disclosure does not require modifications to be implemented to the threshold values from their default values. Implementing the present disclosure without modifying diagnostic parameters eases implementation of HFH risk since the physician does not need to modify the IMD threshold. Compared to the intrathoracic impedance alone that is just one component among the set of IMD diagnostic parameters, a scheme using multiple diagnostic parameters improves overall diagnostic accuracy, as shown in Tables 3 and 4. The present disclosure provides dynamic and particularly sensitive HFH risk assessments for ambulatory patients solely using existing data observations parameters sensed through an IMD (CRT-D IMDs). Thresholds for various parameters and corresponding IMD observations were unmodified from existing CRT-D IMDs.

Since the present disclosure relies on presently existing device diagnostics observations, it is unnecessary to modify computer instructions or configuration of the IMD in order to implement method 200. Moreover, data can be acquired between two transmissions sent via telemetry from the IMD to a physician, two in-clinic follow-up visits, or between a transmission sent via telemetry from the IMD and an in-clinic follow-up visit. Still yet another distinction is that prospective HFH risk level is simply based on number of data observations triggered. For example, one data parameter or diagnostic is not accorded greater weight from another diagnostic. Each data parameter is weighted the same as another data parameter. Accordingly, merely counting the number of data observations during a shortened evaluation time period (e.g. 30 days) is useful in order to calculate the prospective HF risk.

Various examples have been described that include determining a patient's prospective HFH risk using data solely obtained from real-time data sensed using an IMD. These examples include techniques for identifying patients with an elevated risk of being re-hospitalized due to heart failure. In addition, an alert of patient risk levels may be remotely delivered to a healthcare professional from multiple different patients for triage and earlier diagnosis and treatment of heart failure before re-hospitalization. In one or more embodiments, the prospective HFH risk can be calculated for each shorter evaluation period in a set of shorter evaluation periods. The prospective HFH risk by determining whether a HFH event(s) occurred in the next 30 days (HFHnext) divided by the total number of evaluations with or without HFH events in next 30 days (Nnext). In yet another embodiment, a method of operation of a medical device system for determining prospective heart failure hospitalization risk is disclosed such that the method includes measuring one or more data observations via one or more electrodes associated with an implanted medical device disposed in a patient's body, each data observation associated with a diagnostic parameter. The detected data observations is automatically stored into memory of the IMD 16 of a patient. A look back period is defined to include a preceding evaluation period and a current evaluation period. Each data observation is counted in a preceding evaluation period to determine a total number of data observations over a pre-specified time. A determination is made as to whether a heart failure hospitalization event occurred in the current evaluation period. The heart failure hospitalization event of the current evaluation period is multiplied by the total number of data observations over a pre-specified time period. The total number of evaluations in the current evaluation period is determined. The total number of evaluations in the current evaluation period is divided into the product for determining a prospective heart failure hospitalization risk. Displayed on a graphical user interface is an overall evaluation period that extends from a preset start time and extends over the set of shorter evaluation periods. The prospective heart failure hospitalization risk for one shorter evaluation period is weighted differently from another shorter evaluation period from the set of evaluation periods. In one or more other embodiments, HFH risk is calculated heart failure hospitalization (HFH) risk is calculated as a number of evaluations with a given number of data observations in a preceding evaluation period and HFH (or no HFH) event in next 30 days divided by a total number of evaluations with HFH (without HFH) in next 30 days.

In one or more embodiments, the HF risk is computed based upon total number of IMD data observations. The HFH event rates and odds were estimated using a generalized estimating equations (GEE) model for the groups with different number of observations. For purposes of this present disclosure, no adjustment was so made for baseline variables (e.g. age, gender, NYHA, history of coronary artery disease, myocardial infarction (MI), AF, diabetes, and hypertension) or baseline medications (e.g. ACE-I/ARB, diuretics, β-blockers, and anti-arrhythmic drugs).

The exemplary systems, methods, and/or graphical user interfaces described herein may be configured to assist a user (e.g., a physician, other medical personnel etc.) in predicting a patient's risk of HF and/or HFH. The medical device system includes an external device (e.g. server etc.) that is accessed when predicting a patient's risk of HFH. The external device has a collection of heart failure patient-related data organized and stored in memory for access through a processor.

Biomarker information can be used for determining heart failure event risk for a patient. Different variables can be combined to predict a patient's risk of a clinical event such as a HFH. In one or more embodiments, an integrated metric obtained by combining all the device variable improves upon each of the individual variables alone for the purpose of predicting a heart failure event.

Integrated heart failure diagnostics can combine information such as heart failure events, symptoms, drug dosages, weight and blood pressure with device parameters to obtain a combined HF risk score using, for example, a Bayesian architecture which is very amenable to including other variables in the model. New parameters can be added to further improve the accuracy of the integrated metric. An example of such a configuration may be seen with respect to U.S. patent application Ser. No. 13/391,376 filed Feb. 20, 2012 entitled "METHOD AND APPARATUS FOR MONITORING TISSUE FLUID CONTENT FOR USE IN AN IMPLANTABLE CARDIAC DEVICE", and assigned to the assignee of the present invention, the disclosure of which is incorporated by reference in its entirety herein. Additionally or alternatively, another example is disclosed in Martin R. Cowie et al., Development And Validation Of An Integrated Diagnostic Algorithm Derived From Parameters Monitored In Implantable Devices For Identifying Patients At Risk For Heart Failure Hospitalizationin An Ambulatory Setting European Heart Journal (2013) 34, 2472-2480 doi:10.1093/eurheartj/eht083, the disclosure of which is incorporated by reference in its entirety herein.

Briefly, a Bayesian belief network combines multiple sources of information to be able to create a discriminator for diagnostic purposes. Utilizing a database, a Bayesian belief network may combine various information stored in the database and then create a discriminator that can provide a recommendation for different therapies. According to the Bayesian belief network methodology know in the art, based on information from the database, a probability$_{evidence|therapy\ response}$ and a probability$_{therapy\ response}$ are available and are used to determine probability$_{therapy\ response|evidence}$. The evidence is derived from device characteristics and patient characteristics detailed above. The one output of the Bayesian belief network with the largest probability for a given set of evidence may be presented on a graphical user interface. The Bayesian belief network is described in greater detail below.

In this disclosure, certain terms are useful to understand before describing the Byaesian belief network. Biochemical markers and/or bioassays that assist in assessing a patient's overall health (e.g. cardio-renal status) are used to predict a HF event. A HF event includes a HF hospitalization, HF related emergency room (ER) visit or out-patient clinic requiring IV-diuretic. More specifically, a HF event involves any event that was treated with IV diuretics, oral diuretics or ultrafiltration to remove excess fluid.

Exemplary biochemical markers and/or bioassays include brain natriuretic peptide (BNP) and NT-proBNP, creatinine, serum K+, serum Na+, hemoglobin/hematocrit, calcium, creatine phosphokinase, troponin, glucose, blood urea nitrogen (BUN), or cystatin C. BNP and NT-proBNP are hormones released by heart in response to volume overload and stretch. Creatinine is continuously produced by breakdown of muscle and cleared by kidneys. An elevation in serum creatinine is a marker of renal dysfunction. Serum K+ is a very tightly regulated electrolyte important for cellular function. Serum Na+ is a very tightly regulated electrolyte important for cellular function. Hemoglobin/Hematocrit is important for oxygen transportation. Calcium is an important second messenger and plays role in muscle contraction. Creatine phosphokinase is a marker of muscle damage. Troponin is a marker for muscle damage. Glucose is a primary source of energy and tightly regulated by the body. Elevated glucose may be indicative of diabetes. Blood urea nitrogen (BUN) is the amount of nitrogen in blood as a measure of renal function. An elevation of BUN is a marker of poor renal function. Cystatin C is produced by all cells with nucleus and removed from the bloodstream by glomerular filtration in the kidneys. An elevated level of Cystatin C is a marker of declining renal function.

Figure 16:
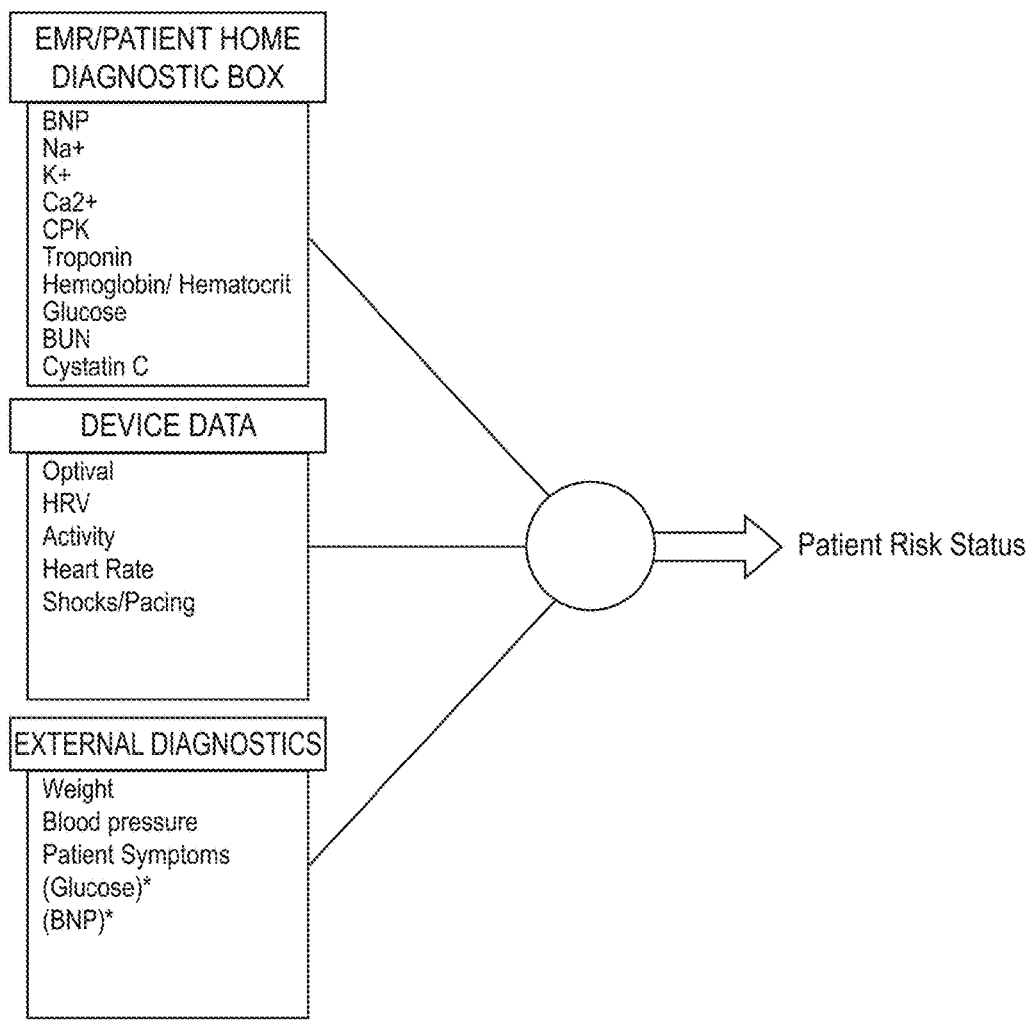
FIG. 16 is a block diagram of data acquired to develop a heart failure event risk status.
Figure 17:
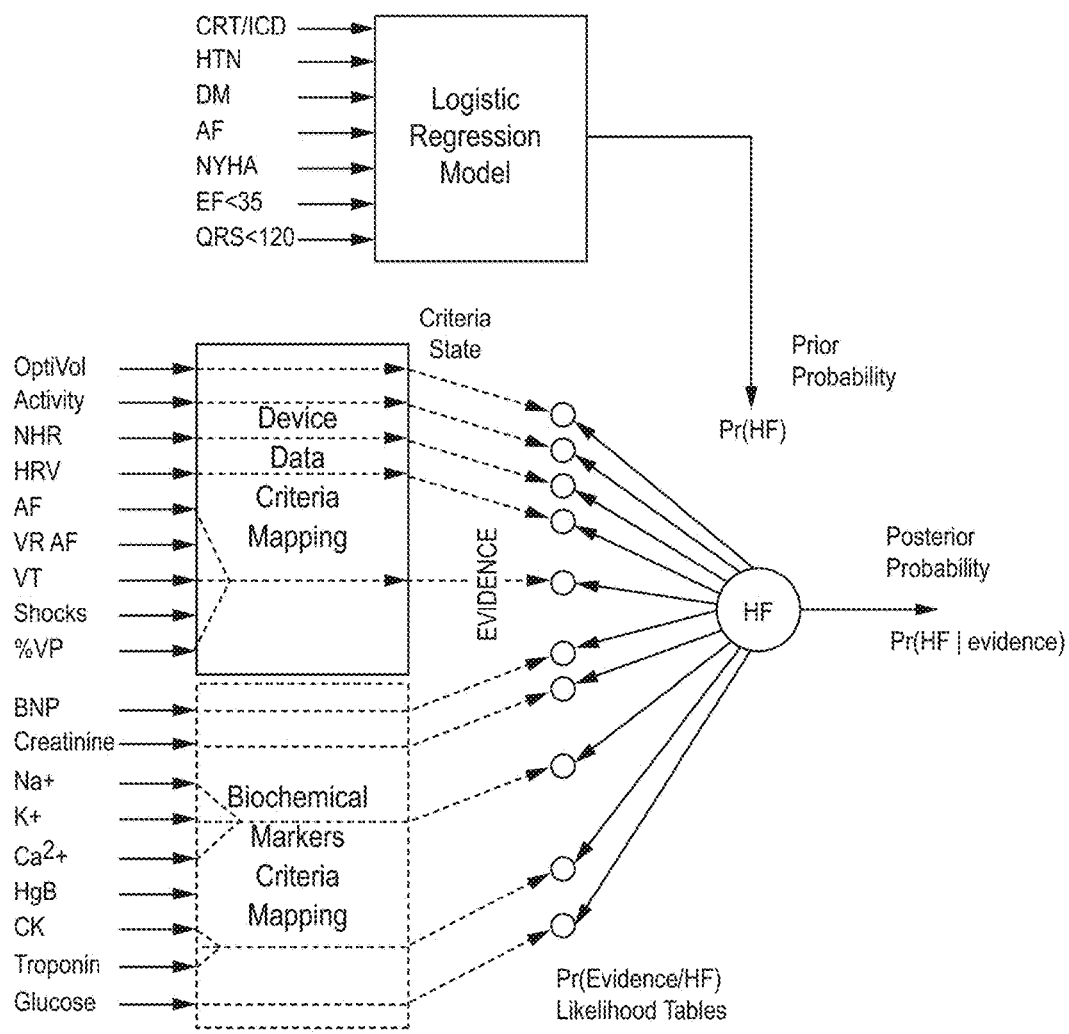
FIG. 17 is a functional illustration of the over-all methodology of generation of the HF risk scores according to the present disclosure.

The results of the bioassays are stored in the Electronic Medical Record (EMR) system that is electronically connected to the CareLink system from Medtronic. CareLink data is output to the EMR. The EMR systems data, related to the exemplary variables (e.g. biochemical markers) listed above, can be incorporated into integrated risk assessment algorithm (FIG. 16). Similar to device variables, various levels can be created of increasing risk. For example, for BNP, more than one risk level (e.g. three risk levels etc.) can be created. Exemplary risk levels are presented below:

Level 1 (Low risk): BNP<100 pg/L
Level 2 (Medium risk): 100 pg/L≥BNP>300 pg/L
Level 3 (High risk): BNP≥300 pg/L Using a similar approach as described herein, risk level thresholds for other biochemical markers can be assigned. Risk level thresholds can then be input into the algorithm, set forth in FIG. 17, to compute HF event risk. FIG. 17 depicts a logistic regression model to determine prior probability, while the device criteria mapping, and biochemical markers criteria mapping are used to obtain the posterior probability of a HF event and/or HFH. Combination of device data, EMR and external diagnostic data can be useful in generating patient risk status for HF event. Essentially, the algorithm assigns criteria state to each variable, and then builds a likelihood table for each variable. This likelihood table links the parameters state to the probability of a HF event or NOT an event. The likelihood tables are then used to create a look up table using Bayesian Belief network that links combinations of various parameter states to a unique HF event probability.

The logistic regression model receives data input from the implanted device (e.g. CRT pacemaker or CRT/ICD), HTN, DM, AF, NYHA, EF less than 35, and/or QRS less than 120. Any regression software can be used such as Matlab regression software. A look-up table is generated from the data, shown in FIG. 16, that is acquired from the device data, external diagnostics. Once the lookup table has been created, an assessment is made of which state each of the parameter is in and then reading off the corresponding probability (HF).

The device data acquired from the IMD can include parameters such as impedance (i.e. OPTIVOL), activity, NHR, HRV, AF, VRAF, VT, whether a shock was delivered, and/or % VP.

The Bayesian Network Based Approach.

A plethora of common statistical approaches could be applied in order to develop an integrated heart failure diagnostic. However, the Bayesian approach has several potential advantages that make it an attractive option for such applications.

The standard Frequentist approach to statistics defines the uncertainty of an event (or random variable A) in terms of the probability of the event happening (or Pr(A)). For example, in order to evaluate the probability of HF (HF) in a patient with CRT-D devices in 12 months, one would count the number of patients having HF in a year then divide by the total number of patients to determine the Pr(HF). In the Bayesian approach, the Frequentist approach is augmented to include other available information or evidence to re-estimate Pr(HF) in the present environment (i.e. in the context of the evidence that is available).

For example, assume one wishes to know the probability of HF Decompensation given that the OptiVol fluid index has crossed threshold (Pr(HF|OptiVol). The OptiVol fluid Index crossing threshold does not necessarily imply an impending HFD. Thus, we employ uncertain reasoning, or probabilities, and further apply the Bayesian approach to quantify the probability given the existing current diagnostic evidence.

Using Bayes rule:

$$Pr(HFD|OptiVol)=Pr(OptiVol|HFD)*Pr(HFD)/Pr(OptiVol)$$

Where,
Pr(HFD|OptiVol) is the posteriori belief (or what we want to find)

Pr(OptiVol|HFD) is the likelihood (which we know from prior data or expert knowledge)

Pr(HFD) is the prior belief (which is the prior belief given no evidence)

Pr(OptiVol) is the normalization factor in this case (can be computed from prior data)

Thus we can estimate the posterior belief of HFD given OptiVol evidence using the likelihood ratio of OptiVol evidence being present before HFD and the prior belief of HFD normalized by the probability of the OptiVol evidence. One aesthetic advantage of this approach is that it is analogous to how the human brain "thinks"; the Bayesian approach just formalizes that approach in a mathematical framework.

When there are multiple variables involved, Bayes' rule may be expanded. The posterior probability computations will then involve computing joint probability distributions and defining multiple combinations of conditional probabilities. One limitation to more broad application of Bayesian probability is that computation of the joint and conditional probability distributions become prohibitive when the number of variables increases. Bayesian Belief network theory addresses that problem by assigning explicit relationships between variables, thereby making the computation more feasible. With explicit defined relationships between variables, only the conditional and joint probabilities for the associated variables need to be defined. Thus Bayesian Belief networks provide a framework for assumptions regarding the explicit relationship between variables to make computation more feasible.

An example of such a configuration may be seen with respect to FIG. 8 of U.S. patent application Ser. No. 13/391,376 filed Feb. 20, 2012 entitled "METHOD AND APPARATUS FOR MONITORING TISSUE FLUID CONTENT FOR USE IN AN IMPLANTABLE CARDIAC DEVICE", and assigned to the assignee of the present invention, the disclosure of which is incorporated by reference in its entirety herein. The Bayesian Belief Network consists of three variables including HF decompensation (HFD), OptiVol Fluid Index (OFI), and Night Heart Rate (NHR). The explicit causal relationship that is assumed in this network is that HFD may cause both OFI changes and NHR changes. The goal of this network may be to find Pr(HFD|OFI, NHR) i.e. what is the probability of HFD given evidence about OFI and/or NHR. In addition, it is desirable to find Pr(OFI|NHR) or Pr(NHR|OFI) i.e. what is the probability of OFI if only NHR evidence is available or vice versa.

To obtain Pr(HFD|OFI, NHR), the likelihood and the prior probability needs to be defined for the network. In this example, Pr(OFI|HFD) and Pr(NHR|HFD) are the likelihood estimates, and Pr(HFD) being the a priori probability of HFD, which needs to be defined based on prior data or expert knowledge. The likelihood estimates can be defined in form of continuous probability distributions as shown in FIG. 8. However, for easier computation, the likelihood estimates can be defined as conditional probability tables. Each of the variables OFI and NHR can be converted to discrete states. For example, OFI can be discretized to five ranges of values [LOW, Medium LOW, MEDIUM, Medium HIGH, HIGH] and the conditional probability table simplifies to the table illustrated in FIG. 9.

Each value in the table of FIG. 9 represents the probability the OFI is in one of the five states given HFD is known to be true or false. Note, that by rules of probability, the sum for each row should be 1. Similarly, NHR can be discretized to 3 ranges of values [LOW, MEDIUM, HIGH] and to the simplified conditional probability table illustrated in FIG. 10.

The basic three variable networks can be expanded to larger numbers of variables. So, for the integrated diagnostics problem, we want to know Pr(HFD|Optivol, NHR, HRV, Activity, AF, VT/NF, %VP, BNP, creatinine, Na+, K+, $Ca^{2+}$, HgB, CK, Tropinin, and glucose). Therefore, we expand the Bayesian Belief network (BBN) so to a 16 variable network. The basic assumptions made to define the network are HFD may cause all the other variables to change, HFD is causally linked to all the other variables. All the other variables are conditionally dependent on HFD, i.e. if there is evidence of HFD (either TRUE or FALSE), then the other variables are associated with each other, otherwise they are independent of each other, i.e. the other variables are not linked to each other but are only linked through HFD.

Any Bayesian network problem may have multiple realizations of a BBN depending on the prior assumptions. For example, a high NHR may cause AT/AF or VT/VF independent of the HF condition, but, for this specific model realization, it is assumed that this cannot be the case. However, this basic BBN can be upgraded to incorporate those dependencies.

Similar to the three variable examples, for this BBN network the conditional probabilities for the additional variables need to be specified. Additionally we need to specify Pr(Activity|HFD), Pr(HRV|HFD), Pr(BNP|HFD), etc. All conditional probabilities can be derived using either prior data or expert knowledge. Thus, when we obtain evidence on the state of the different variables, that is input in the network and the BBN applies that information through the entire network. For example, if we only have OptiVol evidence, this updates the Pr(HFD) and since all the other variables are linked to HFD, the probability for those other variables are also updated if the evidence regarding them are not present. Similarly, if BNP information is not available because the patient did not take a BNP measurement, then the information that OptiVol is HIGH also increases the probability that BNP is also HIGH assuming that the conditional probability tables defines that for both OptiVol and BNP being HIGH increases the probability of HFD.

Defining the Prior Probability

Multiple existing clinical databases can be used to determine the baseline variables that are associated with the HF event. All available baseline variables are used in a univariate and multivariate logistic regression. The baseline variables collected at the beginning of a study can be used as the independent variables, and all HF events in the first 6 months can be used as the dependent variables in the so multivariate logistic regression model. The multivariate logistic regression model fits the data and identifies the independent predictors of HFD events. Some known risk factors are always included in the model irrespective of statistical significance.

The parameters that were used in the model included Age, Sex, Weight, Height, body mass index (BMI), NYHA, ejection fraction (EF), QRS duration, Ischemic Etiology, CRT/ICD device, Hypertension, atrial arrhythmias (AF), Diabetes, coronary artery disease (CAD), MI, LBBB, RBBB, bradycardia, sinus node disease (SND). Notable exclusions from the model are baseline medications which are known predictors of HFD. These parameters were excluded because of unavailability of data.

The logistic regression model generates the list of independent predictors and a baseline probability table. The probability table lists all possible combination of the selected baseline parameters as well as the associated probability of a HFD event in the first six months. The generated baseline probability table from the CONNECT study is used as the prior probability Pr(HFD) for evaluating all the studies. Thus, for each patient, the states for each of the selected baseline parameters are determined from Case Report Forms. The prior probability Pr(HFD) for the patient is determined by table look up from the baseline probability table, i.e., a given set of states for all the selected baseline parameters will correspond to one particular row of the baseline probability tables from which the Pr(HFD) is determined.

Defining the Likelihood Tables

The likelihood tables for the device variables are defined based on the data from the development set. The development set comprised of the following: 1. All patients from the OFISSER study; 2. Patients from the Italian Clinical Services with OptiVol feature in "Observation Only" mode; 3. Patients from the CONNECT study who had a CRT device Each set of individual patient data is divided into 30 day periods beginning 60 days after implant. For each 30-day period, all the diagnostic variable criteria were computed. Diagnostic variable criteria map the raw diagnostic variable data into discrete risk or criteria states. One criterion state is assigned for each variable with precedence given to a "risky" state. For example, if for any day during the 30 day period, OptiVol met the condition for criteria state 4 then the criteria state of 4 is assigned for the OptiVol diagnostic for that 30-day period irrespective of whether any other criteria state was met during that 30-day period. For each 30-day period it was also evaluated whether an HFD event occurred within the next 30-day period. Thus, the likelihood ratios could be computed as Pr(Diagnostic=Criteria State|HFD=False in the next 30 day period)=Number of 30-day period with "Diagnostic=Criteria State" and the following 30-day period without a HFD event/Total number of 30-day periods without a HFD event.

Similarly, Pr(Diagnostic=Criteria State|HFD=True in the next 30 day period)=Number of 30-day period with "Diagnostic=Criteria State" and the following 30-day period with a HFD event/Total number of 30-day periods with a HFD event. Therefore, the conditional probability table or the likelihood tables can be computed for each criteria state for each diagnostic variable.

Generating the BBN Probability Tables

The likelihood tables defined for each criteria state for each diagnostic variable are then provided as input to the Bayesian Belief Network model implemented in the BBN toolbox in Matlab. The BBN model then can provide the posterior probability of Pr(HFD|Diagnostic variable=Criteria State). This posterior probability is then tabulated for all possible combinations of Diagnostic variable and Criteria State to create the BBN Probability tables. Once the criteria state for each diagnostic variable is assigned, the posterior probability is determined from the BBN probability tables. An exemplary scheme for generating the BBN probability tables that can be applied to the present disclosure is shown in FIG. 11 of U.S. patent application Ser. No. 13/391,376 filed Feb. 20, 2012.

In summary, 1. Prior probabilities are generated from the baseline and clinical biomarker data; 2. The likelihood tables are generated from data as explained previously; and 3. The BBN tables are generated using the BBN toolbox in Matlab.

The algorithm implementation comprises the following steps as outlined in the schematic shown in FIG. 17: 1. Generating prior probability estimate and selecting corresponding BBN table; 2. Criteria State Mapping; and 3. Generating posterior probability.

Generating Prior Probability Estimate and Selecting Corresponding BBN Table

The states of the baseline, or static, variables are to be obtained for each patient at implant. The baseline information is used to look up the prior probability from the baseline probability table. The prior probability is categorized into four possible values (e.g. 0.1, 0.15, 0.20, 0.25). This process limits the number of BBN probability tables to be used. The table of FIG. 13 describes this categorization. The corresponding BBN table is selected based on the categorized prior probability estimate.

Criteria State Mapping

Criteria state mapping for device data can be collected in the long term clinical trends (cardiac compass) was performed per the logic illustrated, for example, with respect to U.S. patent application Ser. No. 13/391,376 filed Feb. 20, 2012 entitled "METHOD AND APPARATUS FOR MONITORING TISSUE FLUID CONTENT FOR USE IN AN IMPLANTABLE CARDIAC DEVICE"

Additional Computation for Activity, NHR, and HRV

The three parameters need additional computations which are similar to computation of the OptiVol Fluid Index. The purpose of these computations was to establish whether these parameters increased or decreased over a period of time. All the computation for the above three parameters are similar.

The word PARAM will be used for following description of the computations.

Average PARAM is computed every day as the average of last 7 days of PARAM values. Average PARAM can be computed only if 4 out of the last 7 days have valid measurements else it is undetermined.

Long term average PARAM for a given day is computed as the average of 4 average PARAM values of the present day, present day−7 days, present day−14 days, and present day−21 days. The increase or decrease of the long term average PARAM is limited to DRIFT DOWN and DRIFT UP. Long term average PARAM can be only be computed if average PARAM can be computed for at least one day in the last 14 days else it is undetermined.

Daily Difference PARAM for a given day is the difference between the long term average PARAM and the average PARAM. If average PARAM is undetermined then daily difference PARAM is also undetermined.

Positive difference count is incremented on days long term average PARAM is =average PARAM. It is reset to 0 if daily difference PARAM changes sign and daily difference PARAM is =0. It is also reset to 0 if negative difference count reaches 4 and positive difference count is not equal to 4. If both positive and negative difference count is 4 then positive difference count is reset if daily difference PARAM is <0.

Negative difference count is incremented on days long term average PARAM is <average PARAM. It is reset to 0 if daily difference PARAM changes sign and daily difference PARAM is <0. It is also reset to 0 if positive difference count reaches 4 and negative difference count is not equal to 4. If both positive and negative difference count is 4 then negative difference count is reset if daily difference PARAM is =0.

PARAM Positive Accumulated Difference is the sum of daily difference PARAM for a period of the last positive difference count days. If positive difference count is >14 then accumulation is done only for the last 14 days. PARAM Positive Accumulated Difference has a minimum value of 0.

PARAM Negative Accumulated Difference is the sum of daily difference PARAM for a period of the last negative difference count days. If negative difference count is >14 then accumulation is done only for the last 14 days. PARAM Negative Accumulated Difference has a maximum value of 0.

PARAM Positive Accumulated Difference=PARAM Positive Threshold or PARAM Negative Accumulated Difference=PARAM Negative Threshold (depending on the parameter as listed in the table below) for setting the criteria state for the respective parameters.

PARAM Positive Threshold is equal to Long term average PARAM*Threshold Factor. PARAM Positive Threshold cannot be less that Threshold Floor or greater than Threshold Ceiling.

PARAM Negative Threshold is equal to Long term average PARAM*Threshold Factor. PARAM Positive Threshold cannot be less that Threshold Floor or greater than Threshold Ceiling.

Criteria state mapping for clinical variables collected using patient management system is performed as per the logic described in the table illustrated in FIG. 16 with respect to U.S. patent application Ser. No. 13/391,376 filed Feb. 20, 2012 entitled "METHOD AND APPARATUS FOR MONITORING TISSUE FLUID CONTENT FOR USE IN AN IMPLANTABLE CARDIAC DEVICE."

Generating Posterior Probability

The criteria state information is used to look-up the posterior probability from the selected BBN table. The posterior probability is the HF risk score or the probability of a HF event given all the evidence (or criteria states) for the different device diagnostic variables and biomarker variables. At implant, the HF risk score will be same as the baseline probability which is the risk for a HF hospitalization in the next six months. Every month the HF risk score is updated (or whenever the user chooses to assess the HF risk) based on diagnostic data from the previous month to indicate whether the imminent risk for a HF event has increased or decreased from the baseline risk in the patient. Thus, the baseline HF risk score is the overall (static) risk over a longer time frame, while the month-to-month or risk assessed at user defined time points HF risk score will be able to provide time-varying (dynamic) information regarding the time period during which the patient is more likely to have an event. The variation of the resultant HF Risk Score for an exemplary patient over a 10 month period is displayed on a graphical user interface.

The HF risk score can be computed in two ways.

1. Maximum of Daily Scores: For each day, the HF risk score is calculated based on the criteria states on that day. On the follow-up day, the maximum HF risk score during the past 30 days is used as the risk score at follow-up. A high HF risk score requires multiple diagnostic criteria to be met at the same time.

2. Monthly Score: For each day only the criteria states are evaluated. On the follow-up day criteria states on the last 30 days are evaluated and the riskiest state on any given day on the last 30 days is assigned as the criteria state at follow-up. A HF risk score is then computed based on the criteria state assigned at follow-up based on the criteria state in the last 30 days. A high risk score does not need multiple diagnostic criteria to be met on the same day, but needs multiple criteria to be met in a 30 day time frame. This allows for one diagnostic criteria being a cause for another criteria to be met at a future date.

Figure 18:
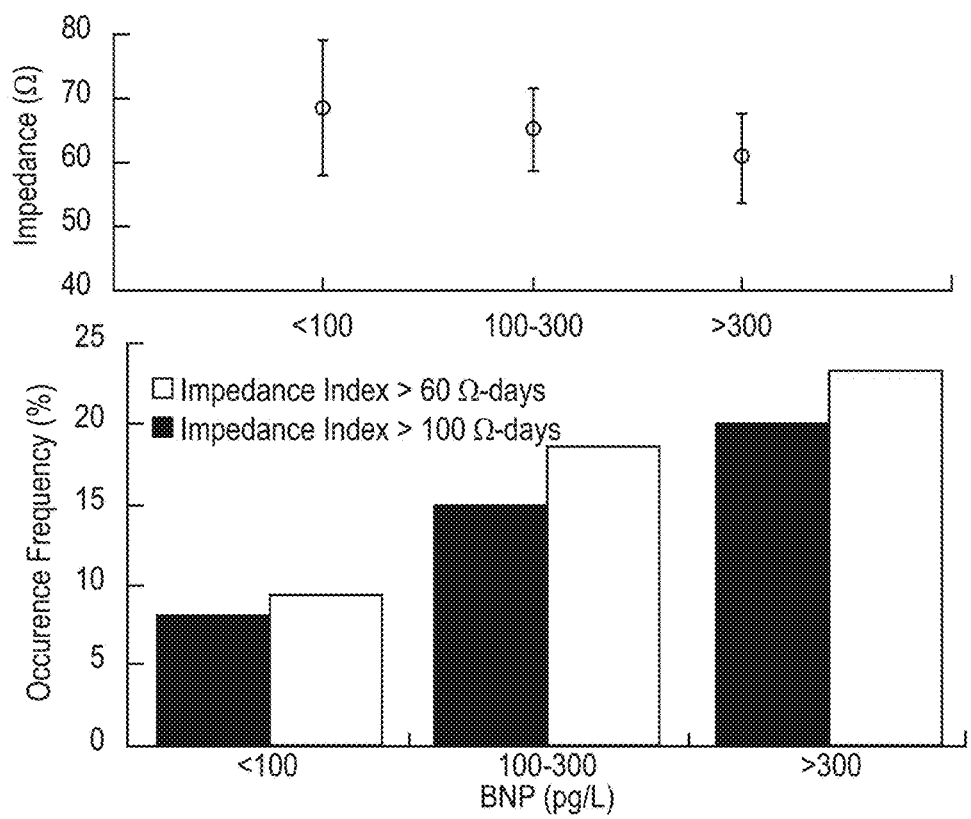
FIG. 18 depicts impedance and occurrence frequency of brain natriuretic peptide (BNP) levels.
Figure 19:
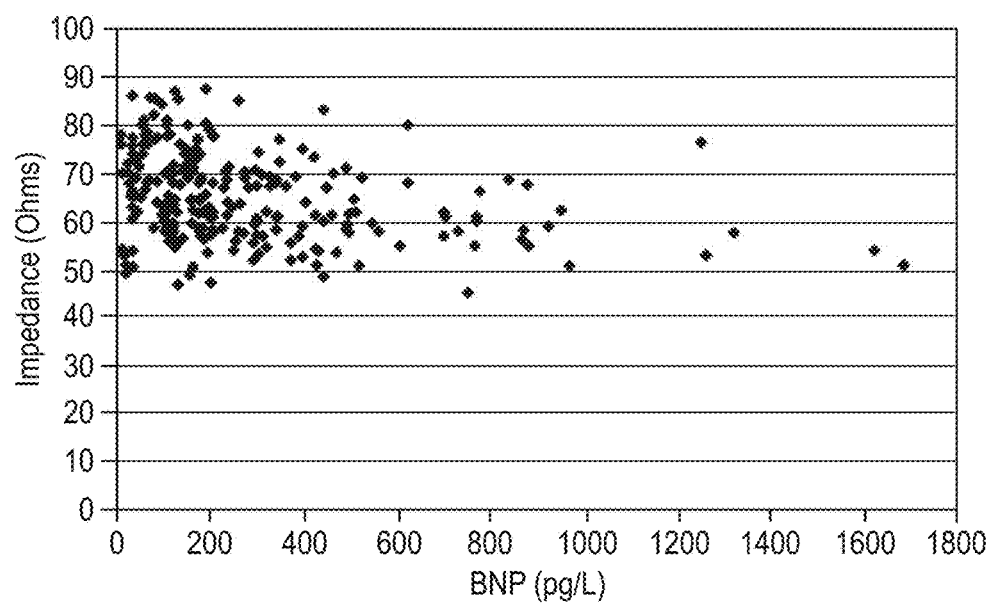
FIG. 19 is a scatter plot correlating impedance and BNP for a patient.

An exemplary patient case is shown in FIGS. 18-19.

Listed below are exemplary biochemical markers for criteria mapping that can be obtained from device data and/or through lab data acquired during a visit to the hospital.

Brain Natriuretic Peptide (BNP) and NT-proBNP is a hormone released by a heart in response to volume overload and strain (i.e. heart muscle stretching or getting physically longer under the applied force).

Creatinine is constantly produced by breakdown of muscle and cleared by kidneys. An elevation in serum creatinine is a marker of renal dysfunction.

Serum K+ is a very tightly regulated electrolyte important for cellular function.

Serum Na+ is a very tightly regulated electrolyte important for cellular function.

Hemoglobin/Hematocrit is important for oxygen transportation.

Calcium is an important second messenger and plays role in muscle contraction.

Creatine phosphokinase is a marker of muscle damage.

Troponin is a marker for muscle damage.

Glucose is a primary source of energy and tightly regulated by body. Elevated in diabetes.

Blood Urea Nitrogen (BUN): Amount of nitrogen in blood as a measure of renal function. An elevation of BUN is a marker of poor renal function.

Cystatin C: Cystatin C is produced by all cells with nucleus and removed from the bloodstream by glomerular filtration in the kidneys. An elevated level of Cystatin C is a marker of declining renal function.

In an exemplary implementation, the availability of the biochemical assay can be sporadically reported depending on patient visits to the clinic. However, since the algorithm performs a look back operation for duration (i.e. currently set at 30 days), even limited information can be integrated into the algorithm and will be of value.

In addition to risk levels associated with the absolute values of BNP, a relative change can be used to determine the patients' risk level. The relative changes may be more effective in indicating the effect of therapy as a decrease in BNP may correlate with an improvement in symptoms of congestion. For example, many patients with acute heart failure syndrome (AHFS) presented at admission to hospital with BNP values much higher than aforementioned threshold values (>>500 pg/L). Once treated, their BNP values drop, but may not still be in the desirable range. However, the data collected could be valuable in managing patients during this vulnerable period (post-acute). In this implementation scheme, physicians will be able to set the range of normal and abnormal ranges of BNP, which will then be combined with other device and non-variables to compute patient's risk of experiencing worsening HF symptoms.

In an alternative implementation, a home based monitor or patient box for the biomarkers such as BNP and glucose could be used to transmit daily data that could be used by the HF risk assessment algorithm. In such implementation, some of the biochemical markers will be combined with device data on a daily basis to compute HF risk for that specific day. The daily data would then be used to compute a longer term risk.

Although a Bayesian scheme can be used, a simpler heuristic non-Bayesian scheme can also be used. Additionally, impedance tends to be lower in patients with higher BNP. This makes mechanistic sense from a physiological viewpoint since sicker patients with higher BNP will tend to have higher incidence/duration of lung congestion, and hence will have lower impedance, as is shown in FIG. 18).

A strong correlation may not be present between BNP and impedance, as shown in FIG. 19. However, BNP and impedance have orthogonal information and hence can be combined to obtain a more robust HF risk marker. Orthogonal information is data that is not correlated i.e. new information that is not already embedded in existing parameters.

FIG. 19 depicts the relationship between BNP and Impedance. Patients with higher BNP levels have lower impedance and greater occurrence of OptiVol crossings over the follow-up duration.

One or more embodiments relate to Hospitalizations in RAFT for Bayesian HFRS Model. Patients with worsening renal function have increasing predisposition to fluid accumulation resulting in lower impedance and more frequent OptiVol crossings, as shown in the figures.

It should be appreciated that prediction of HF event can be accomplished by any one of the methods described herein such as through merely counting all of the observed data observations, as described above. In addition or alternatively, HF event can be predicted using the Bayesian method or any other suitable statistical method.

The following paragraphs enumerated consecutively from 1 through 20 provide for various aspects of the present disclosure. In one embodiment in a first paragraph (1) the present disclosure provides a method of operation of a medical device system for determining prospective heart failure event risk, the method comprising:

1. A method of operation of a medical system for determining prospective heart failure event risk, the method comprising:
   (a) acquiring from a device memory a heart failure patient's current and preceding risk assessment periods;
   (b) counting detected data observations in the current risk assessment period for a current risk assessment total amount and counting detected data observations in the preceding risk assessment period for a preceding risk assessment period total amount;
   (c) associating the current risk assessment and preceding risk assessment total amounts with a lookup table to acquire prospective risk of heart failure (HF) event for the preceding risk assessment period and the current risk assessment period;
   (d) employing weighted sums of the prospective risk of the HF event for the preceding risk assessment period and the current risk assessment period to calculate a weighted prospective risk of the HF event for a patient; and
   (e) displaying on a graphical user interface the weighted prospective risk of the HF event for the patient.

2. The method of paragraph 1 wherein prospective HF event risk can be predicted in real-time while in an ambulatory setting.

3. The method of any of paragraphs 1-2 wherein the lookup table comprises a set of data observations categories and for each said category a stored ratio,
   wherein each said data observations category defines a total number of group data evaluation periods each having a defined same number or falling within a same range of numbers of data observations from a population of patients therein, and
   wherein the stored ratio for each said data observations category comprises a ratio of heart failure hospitalizations associated with the said data observations category to the total number of group evaluation periods within the said data observation category.

4. The method of any of paragraphs 1-3 further comprising: using the prospective risk to modify therapy delivered by an implantable device.

5. A medical system for determining prospective heart failure event risk, the method comprising:
   (a) means for acquiring from a device memory a heart failure patient's current and preceding risk assessment periods;
   (b) means for counting detected data observations in the current risk assessment period for a current risk assessment total amount and counting detected data observations in the preceding risk assessment period for a preceding risk assessment period total amount;
   (c) means for associating the current risk assessment and preceding risk assessment total amounts with a lookup table to acquire prospective risk of heart failure (HF) event for the preceding risk assessment period and the current risk assessment period;
   (d) means for employing weighted sums of the prospective risk of the HF event for the preceding risk assessment period and the current risk assessment period to calculate a weighted prospective risk of the HF event for a patient; and
   (e) displaying means for displaying on a graphical user interface the weighted prospective risk of the HF event for the patient.

6. The system of paragraph 5 wherein prospective HF event risk can be predicted in real-time while in an ambulatory setting.

7. The system of any of paragraphs 5-6 wherein the lookup table comprises a set of data observations categories and for each said category a stored ratio,
   wherein each said data observations category defines a total number of group data evaluation periods each having a defined same number or falling within a same range of numbers of data observations from a population of patients therein, and
   wherein the stored ratio for each said data observations category comprises a ratio of heart failure hospitalizations associated with the said data observations category to the total number of group evaluation periods within the said data observation category.

8. The system of any of paragraphs 5-7 wherein the processor uses the prospective risk to modify therapy delivered by an implantable device.

9. A method of operation of a medical system for determining prospective heart failure event risk, the method comprising:
   (a) acquiring from an implantable medical device memory a heart failure patient's device data;
   (b) acquiring from a memory a heart failure patient's biochemical data;
   (c) calculating a prospective risk of heart failure (HF) event for the patient using the device data and the biochemical marker data; and
   (d) displaying on a graphical user interface the prospective risk of the HF event for the patient.

10. The method of paragraph 9 wherein prospective HF event risk can be predicted in real-time while in an ambulatory setting.

11. The method of any of paragraphs 9-10 wherein prospective HF event risk requires biochemical marker data and device data.

12. The method of any of paragraphs 9-11 wherein the biochemical marker comprises brain natriuretic peptide (BNP), precursor of BNP, N-terminus ProBNP (NT-proBNP), creatinine, serum K+, Serum Na+, hemoglobin, hematocrit, calcium, creatine, phosphokinase, troponin, glucose, blood urea nitrogen (BUN), and Cystatin C.

13. A system comprising:
   at least one implantable sensor;
   a processor that:
      monitors multiple parameters associated with worsening heart failure, including at least one parameter received from the sensor from an implanted medical device and biomarker information;
      derives an index of the likelihood of a heart failure event from the multiple diagnostic parameters by using a Bayesian approach; and
   a display responsive to the processor and which displays the derived index.

14. The system of paragraph 13 wherein the biomarker information comprises one of brain natriuretic peptide (BNP), precursor of BNP, N-terminus ProBNP (NT-proBNP), creatinine, serum K+, Serum Na+, hemoglobin, hematocrit, calcium, creatine, phosphokinase, troponin, glucose, blood urea nitrogen (BUN), and Cystatin C.

15. The system of any of paragraphs 13-14 wherein the biomarker information is acquired from a database configured to receive patient data.

16. The system of any of paragraphs 13-15 wherein the biomarker information is obtained from the implanted medical device.

17. The system of any of paragraphs 13-16 wherein therapy delivered to a patient is modified in response to the derived index.

18. A system comprising:
   at least one implantable sensor;
   a processor that:
      monitors multiple parameters associated with worsening heart failure, including at least one parameter received from the sensor from an implanted medical device and biomarker information, wherein the biomarker information comprises one of brain natriuretic peptide (BNP), precursor of BNP, N-terminus ProBNP (NT-proBNP), creatinine, serum K+, Serum Na+, hemoglobin, hematocrit, calcium, creatine, phosphokinase, troponin, glucose, blood urea nitrogen (BUN), and Cystatin C;
      derives an index of the likelihood of a heart failure event from the multiple diagnostic parameters by using a Bayesian approach; and
   a display responsive to the processor and which displays the derived index.

19. A medical system for determining prospective heart failure event risk, the system comprising:
   (a) means for acquiring from an implantable medical device memory a heart failure patient's device data;
   (b) means for acquiring from the implantable medical device memory a heart failure patient's biochemical data;
   (c) means for calculating a prospective risk of heart failure (HF) event for the patient using the device data and the biochemical marker data; and
   (d) means for displaying on a graphical user interface the prospective risk of the HF event for the patient.

20. The system of paragraph 19 wherein the prospective HF event risk can be predicted in real-time while in an ambulatory setting.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A method of operation of a medical system for determining prospective heart failure event risk, the method comprising:
   (a) acquiring from a device memory a heart failure patient's current and preceding risk assessment periods;
   (b) counting detected data observations in the current risk assessment period for a current risk assessment total amount and counting detected data observations in the preceding risk assessment period for a preceding risk assessment period total amount;
   (c) associating the current risk assessment and preceding risk assessment total amounts with a lookup table to acquire prospective risk of heart failure (HF) event for the preceding risk assessment period and the current risk assessment period;
   (d) employing weighted sums of the prospective risk of the HF event for the preceding risk assessment period and the current risk assessment period to calculate a weighted prospective risk of the HF event for the patient;
   (e) using the prospective risk to modify therapy delivered by an implantable device; and
   (f) delivering the modified therapy to the patient using the implantable device.

2. The method of claim 1 wherein the weighted prospective HF event risk is calculated in real-time while the patient is ambulatory.

3. The method of claim 1 wherein the lookup table comprises a set of data observations categories and for each said category a stored ratio,
   wherein each said data observations category defines a total number of group data evaluation periods each having a defined same number or falling within a same range of numbers of data observations from a population of patients therein, and
   wherein the stored ratio for each said data observations category comprises a ratio of heart failure hospitalizations associated with the said data observations category to the total number of group evaluation periods within the said data observation category.

4. A medical system for determining prospective heart failure event risk, the system comprising:
   (a) means for acquiring from a device memory a heart failure patient's current and preceding risk assessment periods;
   (b) means for counting detected data observations in the current risk assessment period for a current risk assessment total amount and counting detected data observations in the preceding risk assessment period for a preceding risk assessment period total amount;
   (c) means for associating the current risk assessment and preceding risk assessment total amounts with a lookup table to acquire prospective risk of heart failure (HF) event for the preceding risk assessment period and the current risk assessment period;
   (d) means for employing weighted sums of the prospective risk of the HF event for the preceding risk assessment period and the current risk assessment period to calculate a weighted prospective risk of the HF event for the patient;

(e) means for using the prospective risk to modify therapy delivered by an implantable device; and (f) means for delivering the modified therapy to the patient using the implantable device.

5. The system of claim 4 wherein the weighted prospective HF event risk is calculated in real-time while the patient is ambulatory.

6. The system of claim 4 wherein the lookup table comprises a set of data observations categories and for each said category a stored ratio, wherein each said data observations category defines a total number of group data evaluation periods each having a defined same number or falling within a same range of numbers of data observations from a population of patients therein, and wherein the stored ratio for each said data observations category comprises a ratio of heart failure hospitalizations associated with the said data observations category to the total number of group evaluation periods within the said data observation category.

\* \* \* \* \*